US008729136B2

(12) United States Patent
Jia et al.

(10) Patent No.: US 8,729,136 B2
(45) Date of Patent: *May 20, 2014

(54) DIARYLALKANES AS POTENT INHIBITORS OF BINUCLEAR ENZYMES

(71) Applicant: Unigen, Inc., Seattle, WA (US)

(72) Inventors: Qi Jia, Olympia, WA (US); Ji-Fu Zhao, Olympia, WA (US)

(73) Assignee: Unigen, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/707,270

(22) Filed: Dec. 6, 2012

(65) Prior Publication Data

US 2013/0224135 A1   Aug. 29, 2013

Related U.S. Application Data

(60) Division of application No. 12/814,190, filed on Jun. 11, 2010, now Pat. No. 8,592,488, which is a division of application No. 12/027,090, filed on Feb. 6, 2008, now Pat. No. 7,767,661, which is a continuation of application No. 11/139,200, filed on May 27, 2005, now abandoned.

(60) Provisional application No. 60/575,599, filed on May 28, 2004.

(51) Int. Cl.
*A61K 31/75* (2006.01)

(52) U.S. Cl.
USPC .......................................................... 514/721

(58) Field of Classification Search
None
See application file for complete search history.

(56) References Cited

U.S. PATENT DOCUMENTS

| 1,596,613 | A | 8/1926 | Klarmann |
|---|---|---|---|
| 3,133,967 | A | 5/1964 | Ernst et al. |
| 4,678,664 | A | 7/1987 | Schmolka |
| 5,071,835 | A | 12/1991 | Guidon |
| 5,430,062 | A | 7/1995 | Cushman et al. |
| 5,545,399 | A | 8/1996 | Lee et al. |
| 5,719,306 | A | 2/1998 | Chandrakumar et al. |
| 5,880,314 | A | 3/1999 | Shinomiya et al. |
| 6,093,836 | A | 7/2000 | Rhee et al. |
| 6,214,874 | B1 | 4/2001 | Huang et al. |
| 6,221,604 | B1 | 4/2001 | Upadhya et al. |
| 6,296,857 | B1 | 10/2001 | Schonrock et al. |
| 6,355,683 | B1 | 3/2002 | Baell et al. |
| 6,562,791 | B1 | 5/2003 | Maurya et al. |
| 7,767,661 | B2 | 8/2010 | Jia et al. |
| 8,362,305 | B2 | 1/2013 | Nandy et al. |
| 2002/0044914 | A1 | 4/2002 | Dooley et al. |
| 2002/0052410 | A1 | 5/2002 | Steiner et al. |
| 2003/0027810 | A1 | 2/2003 | Efange |
| 2004/0016063 | A1 | 1/2004 | Chassot et al. |
| 2005/0267047 | A1 | 12/2005 | Jia et al. |
| 2006/0178356 | A1 | 8/2006 | Wang et al. |
| 2007/0098655 | A1 | 5/2007 | Schmaus et al. |
| 2008/0032938 | A1 | 2/2008 | Saliou et al. |
| 2010/0267839 | A1 | 10/2010 | Jia et al. |
| 2012/0245393 | A1 | 9/2012 | Nandy et al. |

FOREIGN PATENT DOCUMENTS

| CA | 238730 | A | 3/1924 |
|---|---|---|---|
| CN | 139217 | A | 1/2003 |
| CN | 1439643 | A | 9/2003 |
| CN | 1462739 | A | 12/2003 |
| EP | 0 297 733 | | 1/1989 |
| EP | 1191030 | A2 | 3/2002 |
| EP | 1015446 | | 4/2003 |
| JP | 4906311 | B | 2/1974 |
| JP | 5758610 | A | 4/1982 |
| JP | 05-213729 | A | 8/1993 |
| JP | 08337510 | | 12/1996 |
| JP | 11-255638 | A | 9/1999 |
| JP | 2000/095721 | | 4/2000 |
| JP | 2001-335472 | A | 12/2001 |
| JP | 2002/047132 | A | 2/2002 |
| JP | 2002/193990 | A | 7/2002 |
| JP | 2005-60389 | A | 3/2005 |
| JP | 2005-97144 | A | 4/2005 |

(Continued)

OTHER PUBLICATIONS

Likhitwitayawuid et al., "Chemical transformations of oxyresveratrol (*trans*-2,4,3',5'-tetrahydroxystilbene) into a potent tyrosinase inhibitor and a strong cytotoxic agent," *Bioorganic & Medicinal Chemistry Letters* 16:5650-5653, 2006.

CAPLUS database, "Cosmetics containing stilbene derivatives as tyrosinase inhibitors," Accession No. 2001:873188, 2013, 2 pages.

Klarmann, Emil, "Preparation of 2,4-didydroxydiphenylmethane and of 2,4-dihydroxydiphenylethane," *Journal of the American Chemical Society* 48:791-794, 1926. Database CAPLUS on STN, Acc. No. 1926:9814, 4 pages.

(Continued)

*Primary Examiner* — Craig Ricci
(74) *Attorney, Agent, or Firm* — Seed IP Law Group PLLC

(57) ABSTRACT

The present invention implements a strategy that combines an enzyme inhibition assay with a chemical dereplication process to identify active plant extracts and the particular compounds—diarylalkanes and/or diarylalkanols within those extracts that specifically inhibit binuclear enzyme function. Included in the present invention are compositions of matter comprised of one or more of diarylalkanes and/or diarylalkanols, which inhibit the activity of binuclear enzymes, particularly tyrosinase and which prevent melanin overproduction. The present invention also provides a method for inhibiting the activity of a binuclear enzyme, particularly tyrosinase and a method for preventing and treating diseases and conditions related to binuclear enzyme function. The present invention further includes a method for preventing and treating melanin overproduction and diseases and conditions of the skin related thereto. The method for preventing and treating diseases and conditions related to binuclear enzyme function and melanin overproduction is comprised of administering to a host in need thereof an effective amount of a composition comprising one or more diarylalkanes and/or diarylalkanols synthesized and/or isolated from one or more plants together with a pharmaceutically acceptable carrier.

8 Claims, 15 Drawing Sheets

(56) References Cited

FOREIGN PATENT DOCUMENTS

| | | |
|---|---|---|
| RU | 2156771 C2 | 9/2000 |
| WO | 88/03026 | 5/1988 |
| WO | 88/03800 | 6/1988 |
| WO | 93/23357 | 11/1993 |
| WO | 94/05682 | 3/1994 |
| WO | 98/39279 | 9/1998 |
| WO | 01/30148 | 5/2001 |
| WO | 02/02096 | 1/2002 |
| WO | 02/32379 | 4/2002 |
| WO | 02/34718 | 5/2002 |
| WO | 02/35580 | 5/2002 |
| WO | 03/009807 | 2/2003 |
| WO | 03/040077 | 5/2003 |
| WO | 03/049713 | 6/2003 |
| WO | 03/086414 | 10/2003 |

OTHER PUBLICATIONS

Reimann, Eberhard, "Natural stilbenes. Synthesis of polyhydroxystilbene ethers by the Wittig reaction," *Chemische Berichte* 102(9):2881-2888, 1969. Database CAPLUS on STN, Acc. No. 1969:501457, 1 page.

Da Silva et al., "1,3-Diarylpropanes from *Iryanthera* paraensis and *Iryanthera* tricornis," *Acta Amazonica* 14(3-4):455-457, 1984. Database CALPUS on STN, Acc. No. 1987:15698, 1 page.

Tandon et al., "A bibenzyl xyloside from *Chlorophytum arundinaceum*," *Phytochemistry* 32(6):1624-1625, 1993. Database CAPLUS on STN, Acc. No. 1993:513368, 1 page.

Dol et al., "Binding properties of two novel phosphine-modified tetrapodants and their bimetallic transition metal complexes," *European Journal of Inorganic Chemistry* 12:1975-1985, 1998. Database CAPLUS on STN, Acc. No. 1998:771697, 2 pages.

Ando et al., "Cyclization Reactions of 2,3-Bis (2-Cyanophenyl) Propionitriles. III. Substituent Effect on the Carbanion Reactives of the Propionitriles and Tautomerism of 5-Acetomido-11-Cyanoindeno[L,2-C]Isoquinolines," *Bulletin of the Chemical Society of Japan, Chemical Society of Japan*, 53(10):2885-2890, 1980.

Anjaneyulu et al., "Nordihydroguairetic Acid, A Lignin, Prevents Oxidative Stress and the Development of Diabetic Nephropathy in Rats," *Pharmacology* 72(I): 42-50, 2004.

Anonymous, "CGP-61755 (Lasinavir (234416))," *Annual Drug Data Report* 18(6):553, 1996.

Bezuidenhout et al., "hydroxydihydrochalcones and Related 1,3-Diarylpropan-2-ones from *Xanthocercis zambesiaca*," *Phytochem.* 27(7):2329-2334, 1988.

Bohlmann, et al., "Neue Chalkon-Derivate Aus Sudafrikanischen Helichrysum-Arten," *Phytochem* 17:1935-1937, 1978.

Braz F. et al., "Diarylpropanoid from *Virola multinervia*," *Phytochem.* 15:567-568, 1976.

Braz Filho et al., "Flavonoids from *Iryanthera* Laevis," *Phytochem.* 19:1195-1197, 1980.

Calas et al., "Synthese d'analogues noveaux de la trimethoprime Etude de relation structure-activite antibacterienne," *Eur. J. of Med. Chem.* 17(6):497-504, 1982.

Carpenter et al., "Synthesis of Molecular Units for Rational Synthesis of Phenol-Formaldehyde and Allied Resins. I. Synthesis of Resoles, Dihydroxydiphenylethanes, and Dihydroxydiphenylpropanes," *J. Appl. Chem.* 1:217-226, 1951.

De Almeida et al., "Diarylpropanoids from *Iryanthera* Polynerua," *Phytochem.* 18:1015-1016, 1979.

Diaz D. et al., "Diarylpropanes from the Wood of *Iryanthera* Grandis," *Phytochem.* 25(10):2395-2397, 1986.

Gonzalez et al., "Stilbenes and other Constituents of *Knema austrosiamensis*," *Phytochem.* 32(2):433-438, 1993.

Goodson et al., "Analgesics. III. Hydrochlorides of Phenylalkylamines," *Journal of the American Chemical Society* 71(9):3219-3221, 1949.

Hagos et al., "Isolation of Smooth Muscle Relaxing 1,3-Diarylpropan-2-ol Derivatives from *Acacia tortilis*," *Planta Med.* 53:27-31, 1987.

Iida et al., "Sensitive Screening of Antfungal Compounds from Acetone Extracts of Medicinal Plants with a Bio-Cell Tracer," *Yakugaku Zasshi* 119:964-971, 1999.

Ikota et al., "Components of *Broussonetia kazinoki* SIEB. I. Structure of Two New Isoprenylatd Flavans and Five New Isoprenylated 1,3-Diphenylpropane Derivatives," *Chem. Pharm. Bull.* 34:1968-1979, 1986.

Jang et al., "Melanogenesis Inhibitor from paper Mulberry," *Cosmetics & Toiletries* 112:59-62, 1997.

Jia et al., "Diarylpropanes as a novel class of potent tyrosinase inhibitors and their biological properties," *Journal of Investigative Dermatology* 127(suppl. 1):S151, 2007.

Kato et al., "Components of *Broussonetia kazinoki* SIEB. (2). Structures of Four New Isoprenylated 1,3-Diphenylpropane Derivatives," *Chem Pharm. Bull* 34:2448-2455, 1986.

Kijjoa et al., "1,3-Diaryl-Propanes and Propan-2-ols from *Virola* Species," *Phytochem.* 20(6):1385-1388, 1981.

Ko et al., "Cytotoxic Isoprenylated Flavans of *Broussonetia kazinoki*," *J. Nat. Prod.* 62:164-166, 1999.

Kuck et al., "Hydrogen Rearrangement in Molecular Ions of Alkyl Benzenes: Mechanism and Time Dependence of Hydrogen Migrations in Molecular Ions of 1,3-Diphenylpropane and Deuterated Analogues," *Organic Mass Spectrometry* 13(2):90-102, 1978.

Lee et al., "Aromatase Inhibitors from *Broussonetia paprifera*," *J. Nat. Prod.* 64:1286-1293, 2001.

Lee et al., "Hydrogen-Deuterium Exchanges in a Friedel-Crafts Reaction," *Journal of Organic Chemistry* 50:705-707, 1985.

Leong et al., "1-(2-Hydroxy-3,4,5,6-Tetramethoxyphenyl)-3-Phenylpropene From *Lindera lucida*," *Phytochemistry* 49(7):2141-2143, 1998.

Lin et al., "Phenolic Glycosides from *Viscum* anagulatum," *J. Nat. Prod.* 65:638-040, 2002.

Matubara et al , "Inhibitory effect of Lichen Metabolites and Their Synthetic Analogs on Melanin Biosynthesis in Cultured B-16 Mouse Melanoma Cells," *Natural Product Sciences* 4(3):161-169, 1998.

Maurya et al., "The Synthesis of Propetrol, a Novel 1,3-Diarylpropan-2-ol from *Pterocarpus marsupium*," *J. Nat. Prod.* 48(2):313-315, 1985.

Morimoto et al., "Tannins and related Compounds. XXIX.1Seven New Methyl Derivatives of Flavan-3-ols and 1,3-Diarylpropane-2-ol from *Cinnamomum cassia*, *C. obtusifolium* and *Lindera umbellate* var. membranacea," *Chem. Pharm. Bull.* 33:2281-2286, 1985.

Morais, et al., "Synthesis of Three Natural 1,3-Diarylpropanes: Two Revised Structures," *Phytochemistry* 28(1):239-242, 1989.

Moss et al., "Peptidomimetic Inhibitors of herpes Simplex Virus Ribonucleotide Reductase: A New Class of Antiviral Agents," *Journal of Medicinal Chemistry* 38(18):3617-3623, 1995.

Nandy et al., "A convenient method for the syntheses of tetrahydrofuran moiety from furan by catalytic transfer of hydrogenation with ammonium formate," *Tetrahedron Letters* 49:2469-2471, 2008.

Nandy et al., "Series of Skin Whitening (Lightening) Compounds," filed Dec. 20, 2012, for U.S. Appl. No. 13/722,394, 60 pages.

Napolitano et al , "Inhibitory effect of melanin precursors on arachidonic acid peroxidation," *Biochimica et Biophysica Acta* 1168:175-180, 1993, 7 pages.

Ohguchi et al., "Effects of Hydroxystilbene Derivatives on Tyrosinase Activity," *Biochemical and Biophysical Research Communications* 307(4):861-863, 2003.

Ohguchi et al , "Inhibitory Effects of Resveratrol Derivatives from Dipterocarpaceae Plants on Tyrosinase Activity," *Bioscience, Biotechnology and Biochemistry* 67(7):1587-1589, 2003.

Pettit et al., "Antineoplastic Agents 440. Asymmetric Synthesis and Evaluation of the Combretastatin A-I SAR Probes (1S,2S)-And (1R,2R)-1,2-Dihydroxy-1-(2',3'-dihydroxy-4'-methoxyphenyl)-2(3",4",5"-trimethoxyphennyl)-ethane," *Journal of Natural Products* 63(7):969-974, 2000.

Rao et al., "Propterol: A 1,3-Diarylpropan-2—ol from *Pterocarpus marsupium*," *Phytochemistry* 23(4):897-898, 1984.

Shimizu et al , "Inhibition of Tyrosinase by Flavonoids, Stilbenes and Related 4-Substituted Resorcinols: Structure-Activity Investigations," *Planta Medica* 66(I):11-15, 2000.

(56) References Cited

OTHER PUBLICATIONS

Silva et al., "Dihydrochalcones and Flavonolignans from *Iryanthera lancifolia*," *J. Nat. Prod.* 62(11)1475-1478, 1999.

Stedman's Medical Dictionary: "Melanin," Twenty-Second Edition, p. 755, col. 2, lines 16-25, 1972.

Stuart et al., "2,4-Diamino-5-Benzylpyrimidineasn and Analogues as Antibacterial Agents. 6. A One-Step Synthesis of New Trimethoprim Derivatives and Activity Analysis by Molecular Modeling," *Journal of Medicinal Chemistry* 26(5):667-673, 1983.

Takasugi et al., "Eight Minor Phytoalexins from Diseased paper Mulberry," *Chem Lett.* 689-692, 1984.

Talukdar et al., "An isoflavone from *Myristica malabarica*," *Phytochemistry* 53:155-157, 2000.

Tsuchiya et al., "Anti-Candida Activity of Synthetic Hydroxychalcones," *Die Pharmazie* 49(10):756-758, 1994.

Williams and Lemke, Foyes' Principles of Medicinal Chemistry, Fifth Ed., 60-61, 2002, 14 pages.

Wu et al., "Total Synthesis of Nordihydroguaiaretic Acid," *Acat Pharmaceutica Sinica* 32(4):278-281, 1997. (abstract).

Yoshitomi et al., "Cosmetics Containing Hydrochalcone Glycosides," & JP 2002 193990A (Japan) (Abstract), 2002.

Zeng et al., "Kneglomeratonol, Kneglomeratanones A and B, and Related bioactive Compounds from *Knema glomerata*," *J. Nat. Prod.* 57(3):376-381, 1994.

Office Action issued Apr. 3, 2009 in U.S. Appl. No. 12/027,090.

Office Action issued Jan. 13, 1010, in U.S. Appl. No. 12/027,090.

International Search Report issued Nov. 10, 2005, in International Application Serial No. PCT/US2005/018884.

Written Opinion issued Nov. 10, 2005, in International Application Serial No. PCT/US2005/018884.

EP Search Report issued Nov. 21, 2008 in EP 05762186.4.

International Search Report issued Sep. 16, 2009, in International Application Serial No. PCT/US2009/051217, 2 pages.

International Preliminary Report on Patentability and Written Opinion issued Jan. 25, 2011, in International Application Serial No. PCT/US2009/051217, 9 pages.

Office Action for Canadian Application No. 2,567,801, Nov. 7, 2011.

Notification of First Office Action for corresponding Chinese Patent Application No. 201110080259.8, mailed Mar. 12, 2012.

English translation of Notification of First Office action for corresponding Chinese Patent Application No. 201110080259.8, mailed Mar. 12, 2012.

English Translation of Notification of First Office Action for corresponding Chinese Patent Application No. 200980128510.4, mailed Mar. 22, 2012, 5 pages.

Notification of First office Action for corresponding Chinese Patent Application No. 200980128510.4, mailed Mar. 22, 2012, 4 pages.

International Search Report and Written Opinion issued Aug. 14, 2012, in International Application Serial No. PCT/US2012/029875, 11 pages.

English translation of Japanese Reasons for Rejection for corresponding Japanese Patent Application No. 2007-515432.

Fujikawa et al., "Studies on Antiseptics for Foodstuff. LXXII. Studies on Dipenyl Ether Derivatives Biphenyl Derivatives and Dibenzofuran Derivatives as a Preservative for Sake," *UDC* 91:930-933, 1971.

| Structure | Name | Mechanism of Action | Inhibition Constant |
|---|---|---|---|
| | L-Tyrosine | | |
| 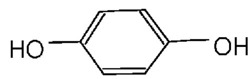 | Hydroquinone | Alternative substrate | $IC_{50} = 75\ \mu M$ |
| 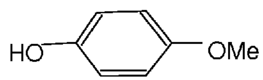 | 4-Hydroxyanisole | Alternative substrate | |
| 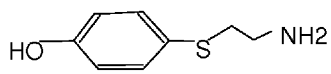 | 4-SCAP | Alternative substrate | |
| 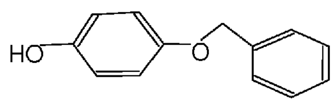 | Monobenzone | Alternative substrate | |
| 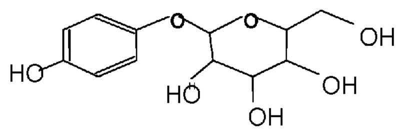 | Arbutin | Hydroquinone pro-drug | $IC_{50} = 17\ mM$ |
| 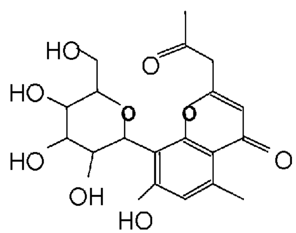 | Aloesin | Competitive inhibition | $IC_{50} = 167\ \mu M$ |

FIG. 3A

| Structure | Name | Mechanism of Action | Inhibition Constant |
|---|---|---|---|
| 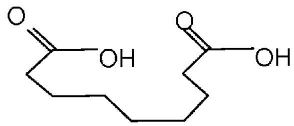 | Azelaic acid | Block tyrosinase to Active site | Ki=0.00273 |
| 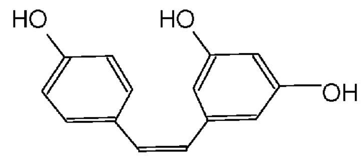 | Resveratrol | Alternative substrate | $IC_{50} = 54\ \mu M$ |
| 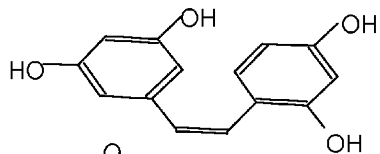 | Oxyresveratrol | Non-competitive inhibitor | $IC_{50} = 1.2\ \mu M$ |
| 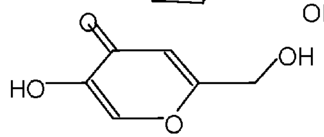 | Kojic acid | Copper chelation | $IC_{50} = 6.2\ \mu M$ |
| 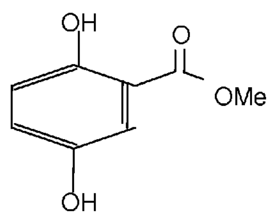 | Methyl Gentisate | Copper chelation | $IC_{50} = 11.2\ \mu M$ |
| 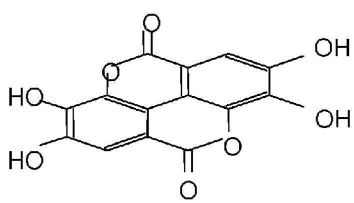 | Ellagic acid | Copper chelation | |

FIG. 3B

DIARYLALKANES AS POTENT INHIBITORS OF BINUCLEAR ENZYMES

RELATED APPLICATIONS

This application is a divisional of U.S. application Ser. No. 12/814,190, filed Jun. 11, 2010, which is a divisional of U.S. application Ser. No. 12/027,090, filed Feb. 6, 2008, now issued as U.S. Pat. No. 7,767,661, which is a continuation of U.S. application Ser. No. 11/139,200, filed May 27, 2005, now abandoned, which claims the benefit under 35 U.S.C. §119(e) of U.S. Provisional Application No. 60/575,599, filed May 28, 2004. Each of these applications is incorporated herein by reference in its entirety.

FIELD OF THE INVENTION

This invention relates generally to the prevention and treatment of diseases and conditions mediated by binuclear enzymes. Specifically, the present invention includes a method for inhibiting the activity of an enzyme having a binuclear active site. Included in the present invention are novel compositions comprised of one or more diarylalkane(s). The diarylalkanes of the present invention can be isolated from one or more plant sources or can be obtained by organic synthesis. Further included in the present invention are methods for isolating these compounds from a natural source and methods for synthesizing these compounds. In one embodiment, the diarylalkanes are obtained by synthetic modification of a naturally occurring compound isolated from a plant source.

BACKGROUND OF THE INVENTION

There is a great demand for products able to inhibit or prevent excessive pigmentation of the skin. Melanin, the skin's natural pigment, is a nitrogenous polymer synthesized in melanosomes, which are membrane-bound organelle present within melanocytes. Melanin is produced in varying concentrations, depending on skin type (genetic disposition) and environmental conditions. Melanocytes are cells that occur in the basal membrane of the epidermis, and account for between 5% and 10% of the cellular content (approximately 1200-1500 melanocytes per cm$^2$). When stimulated, by factors such as ultraviolet (UV) light melanocytes divide more rapidly, thereby producing greater quantities of melanin. The melanin is then transported in mature melanosomes to keratinocytes, within the epidermis where it becomes visible as a brown skin color.

The number of melanocytes in human skin is more or less the same, irrespective of skin color. The color of the skin is largely dependent on the quantity and type of melanin produced (black eumelanin or yellow to reddish-brown pheomelanin). Asians and light-skinned people have lower levels of eumelanin than dark-skinned people, and correspondingly less protection against the effects of radiation. People with red hair are characterized by pigmentation with pheomelanin, and have little or no photo-protection. Additionally, the distribution of melanin in the skin also varies. In people with light skin, the greater part of the pigment lies in the basal layer, whereas in those with dark skin, the melanin is spread throughout, reaching into the horny layer.

The over production of melanin can cause different types of abnormal skin color, hair color and other diseases and conditions of the skin. There are primarily two conditions related to skin pigmentation disorders. A darkening of the skin that includes abnormal elevated melanin caused by UV exposure and aging; and abnormal distribution of skin pigments resulting in age spots, liver spots, and drug and wound/disease induced hyperpigmentation (Seiberg et al. (2000) J. Invest. Dermatol. 115:162; Paine et al. (2001) J. Invest. Dermatol. 116:587).

Modulators of melanogenesis (the production of melanin) may be designed or chosen to function in a variety of ways as illustrated in FIG. 1. With reference to FIG. 1, they may act directly on modulating melanosome structure and function prior to melanin synthesis, they may act by inhibiting the production or function of enzymes, such as tyrosinase, which are involved in the synthesis of melanin, they may changing the ratio of eumelanin/pheomelanin, or they may function by damping mechanisms responsible for transfer of melanosomes from melanocyte to keratinocytes. (Briganti et al. (2003) Pigment Cell Research 16:101-110).

Tyrosinase is a key enzyme in the production of melanin. It catalyzes three reactions: the hydroxylation of tyrosine to 3,4-dihydroxyphenylalanine (DOPA), oxidation of DOPA to DOPA quinone and the oxidation of DHI (5,6-dihydroxyindole) to indole quinone. (Hearing et al. (1991) FASEB 53:515). It has been determined that tyrosinase needs both the substrate and divalent metal ions for its catalytic activity. The processes currently used for inhibiting the synthesis of melanin with a view to lightening skin are primarily based on substances which inhibit tyrosinase activity, either directly by interacting with tyrosinase itself, or indirectly e.g., by complexing the necessary metal ions.

Tyrosinase belongs to the family of type 3 copper proteins, which contain two copper ions at their active site. Studies of the structure of the active site of tyrosinase have revealed that the two copper ions are closely spaced and each ion is coordinated to three histidines through the N-ε nitrogen atom of its side chain, as illustrated in FIG. 2. (Pfiffner and Lerch (1981) Biochem. 20: 6029; Cuff et al. (1998) J. Mol. Biol. 278:855). The binuclear copper ions can exist in three main redox forms: the $Cu^I$—$Cu^I$ reduced form, the $Cu^{II}$—$O_2$—$Cu^{II}$ form which reversibly binds to $O_2$ as the peroxide, and the resting form of the enzyme, where the $Cu^{2+}$ ions are normally bridged by a small ligand. It has been determined that the $Cu^{II}$—$O_2$—$Cu^{II}$ redox state is key to the enzymatic activity of tyrosinase. In this state, tyrosinase catalyzes the introduction of a second hydroxyl group to the ortho position of a monophenol (such as tyrosine) a reaction which is key to the biosynthesis of melanin.

Any compound, which interferes with the access, ligand formation, or the oxidation of monophenols at the active site of tyrosinase, will be an efficient inhibitor of tyrosinase, potentially resulting in a decrease in the production of melanin and lighter skin color. Generally speaking, the copper ions at the active site of tyrosinase can be easily chelated with lone pair electrons on oxygen, nitrogen, sulfur and halogens. (Weder et al. (1999) Inorg. Chem. 38:1736). FIG. 3 illustrates the structures and mechanisms of action of several known tyrosinase inhibitors. (Briganti et al. (2003) Pigment Cell Research 16:101-110; Seo et al. (2003) J. Agric. Food Chem. 51:2837).

With reference to FIG. 3, it can be seen that compounds with structures similar to 3,4-dihydroxyphenylalanine (DOPA), such as hydroquinone, both inhibit tyrosinase and are also melanocytolytic agents. (U.S. Pat. No. 5,523,077). For example, arbutin, isolated from the leaves of the common bearberry, *Uvae ursi*, is a naturally occurring beta-glucopyranoside of hydroquinone, which inhibits tyrosinase and effects melanin synthesis in human melanocytes. (Chakraborty et al. (1998) Pigment Cell Res. 11:206; U.S. Pat. No. 5,980,904). The mechanism of action for arbutin involves competition with L-tyrosine or L-dopa for binding at the active site of tyrosinase. It does not suppress the expression or the synthesis of the protein. (Maeda and Fukuda (1996) J. Pharmacol. Exp. 276:765). Synthetic arbutin type compounds also strongly inhibit human tyrosinase. (Sugimoto et al. (2003) Chem. Pharm. Bull. 51:798). Kinobeon A, a novel diquinone isolated from cultured cells of safflower (*Carthamus tinctorius* L.), has tyrosinase inhibitory activity greater than that of kojic acid. (Kanehira et al. (2003) Planta Med. 69:457). If applied over long periods of time or in high concentrations hydroquinones can have serious side effects. Additionally, hydroquinones may lead to permanent de-pigmentation, and thus to increased photosensitivity of the skin when exposed to UV light.

Better-tolerated skin lightening substances currently being used are of natural origin. For example, kojic acid is a natural hydroxyl-γ-pyrone derived from carbohydrate solutions containing certain bacteria. With reference to FIG. 3, it can be seen that kojic acid is an oxidized ortho-dihydroxyphenol. Kojic acid is known to form strong chelates with metal ions especially $Cu^{II}$. (Gerard and Hugel (1975) Bull. Soc. Chim. Fr. 42:2404). It is a potent competitive, but slow binding inhibitor of tyrosinase. (Cabanes et al. (1994) J. Pharm. Pharmacol. 46:982). Recent studies have shown that kojic acid acts as a bridging ligand, binding strongly to both the dicopper (II) complex and to the dicopper-dioxygen adduct, thereby preventing the binding of the catechol substrate to the enzyme. (Battaini et al. (2000) JBIC 5:262). Kojic acid and its esters have been patented for use as skin whiteners. (see U.S. Pat. Nos. 4,369,174; 4,771,060; 5,824,327; 5,427,775; 4,990,330).

Flavonoids are another class of natural products that have been reported as inhibitors of tyrosinase. (Shimizu et al. (2000) Planta Med. 66:11; Xie et al. (2003) Biochem. 68:487). Active tyrosinase inhibitors include flavones (Likhitwitayawuid et al. (2000) Planta Med. 66:275), flavonols (Kubo and Kinst-Hori (1999) J. Agric. Food Chem. 47:4121), prenylated flavonoids (Kuniyoshi et al. (2002) Planta Med. 68:79; Son et al. (2003) Planta Med. 69:559; Kim et al. (2003) Biol. Pharm. Bull. 26:1348), flavans (No et al. (1999) Life Sci. 65:PL241; Kim et al. (2004) Biomacromolecules 5:474), and dihydro-chalcones (Shoji et al. (1997) Biosci. Biotechnol. Biochem. 61:1963).

Other types of tyrosinase inhibitors include: phenol derivatives (Sakuma et al. (1999) Arch. Pharm. Res. 22:335; Kerry and Rice-Evans (1999) J. Neurochem. 73:247; Battaini et al. (2002) J. Biol. Chem. 277:44606), benzaldehydes (Kubo and Kinst-Hori (1999) Plant Medica 65:19; Chen et al. (2003) J. Enzyme Inhib Med. Chem. 18:491; Nihei et al. (2004) Bioorg. Med. Chem. 14:681), benzoic acid derivatives (Curto et al. (1999) Biochem Pharmacol. 57:663; Chen et al. (2003) J. Protein Chem. 22:607; Miyazawa et al. (2003) J. Agric. Food Chem. 51:9653; Kubo et al. (2003) Z. Naturforsch [C] 58:713), cupferron (Xie et al. (2003) Int. J. Biochem. Cell Biol. 35:1658), benzodipyran from *Glycyrrhiza uralensis* root (Yokota et al. (1998) Pigment Cell Res. 11:335), thiohydroxyl compounds (Park et al. (2003) J. Protein Chem. 22:613), terpenoids (Oh et al. (2002) Planta Med. 68:832), and oxazolodinethione (Seo et al. (1999) Planta Med. 65:683). The most potent known natural tyrosinase inhibitors are stilbenes ($IC_{50}$=0.3-5 μM) (Shin et al. (1998) Biochem Biophys. Res. Commun. 243:801; Ohguchi et al. (2003) Biosci. Biotechnol. Biochem. 67:1587), stilbene glycosides (Lida et al. (1995) Planta Med. 61:425) and 4-substituted resorcinols (Shimizu et al. (2000) Planta Med. 66:11).

A structure/activity study of 4-substituted resorcinols reveals that hydrophobic and less bulky substituents, such as —$CH_2C_6H_5$, and alkyl groups i.e. —$CH_2CH_2CH_3$ have the greatest potency with $IC_{50}$'s of less than 10 μM (Shimizu et al. (2000) Planta Med. 66:11). The mechanism of action for 4-substituted resorcinols has been characterized as slow-binding competitive inhibition of the oxidation of DL-β-(3, 4-dihydroxyphenyl)alanine (DL-dopa) (Jimenez and Garcia-Carmona (1997) J. Agric. Food Chem. 45:2061) without any further understanding of the metal chelating effects on binuclear copper ions.

*Aloe*, a member of the Lily family, is an intricate plant that contains many biologically active substances. (Cohen et al. (1992) in *Wound Healing/Biochemical and Clinical Aspects*, 1st ed. W B Saunders, Philadelphia). Over 360 species of *Aloe* are known, most of which are indigenous to Africa. Historically, *Aloe* products have been used in dermatological applications for the treatment of burns, sores and other wounds. These uses have stimulated a great deal of research in identifying compounds from *Aloe* plants that have clinical activity. (See, e.g., Grindlay and Reynolds (1986) J. of Ethnopharmacology 16:117-151; Hart et al. (1988) J. of Ethnopharmacology 23:61-71).

Yagi et al. disclose a group of compounds isolated from *Aloe*, particularly aloesin and one of its derivatives, 2"-O-feruloylaloesin, which are effective inhibitors of tyrosinase. (Yagi et al. (1987) Plant Medica 515-517; Yagi et al. (1977) Z. Naturforsch 32c:731-734). Aloesin, a C-glucosylated 5-methylchromone inhibited human tyrosinase hydroxylase activity in a dose dependent manner with an $IC_{50}$ of 0.92 mM and also inhibited DOPA oxidase activity in a dose dependent manner with $IC_{50}$=0.70 mM compared to kojic acid, which has an $IC_{50}$=0.41 mM, and arbutin which has an $IC_{50}$=3.02 mM. Inhibition of tyrosinase enzymatic activity and consequent melanin formation by aloesin was confirmed in a cell-based assay using B16 F1 murine melanoma cells. Melanin biosynthesis was inhibited by aloesin ($IC_{50}$=0.167 mM) in a dose dependent manner. (Jones et al. (2002) Pigment. Cell Res. 15:335). The mechanism of action of tyrosinase inhibition for aloe chromones is speculated as being related to the reduction of copper ions. Both natural (U.S. Pat. No. 6,451,357), semi-synthetic (U.S. Pat. Nos. 5,801,256; 6,083,976) and formulated aloe chromones (U.S. Pat. No. 6,123,959) have been patented for their skin whitening ability.

Ascorbic acid (vitamin C from synthetic and natural sources such as citrus fruits) and its derivatives have also been utilized for skin whitening. In most cases, vitamin C is formulated with kojic acid or other tyrosinase inhibitors (U.S. Pat. Nos. 4,919,921; 6,458,379 and 5,916,915). Other reported skin whitening compounds include extracts from olive plants (U.S. Pat. No. 6,682,763), unsaturated long chain fatty acids (U.S. Pat. No. 6,669,932), curcumins (U.S. Pat. No. 6,641,845), enzyme extracts (U.S. Pat. No. 6,514,506), coumestrol (U.S. Pat. No. 6,503,941), hydroxyl carboxylic acids (U.S. Pat. Nos. 6,417,226; 6,365,137; 5,609,875; 5,262, 153), beta-glucans (U.S. Pat. No. 6,251,877), aloe chromones (U.S. Pat. No. 6,083,976), phenylalanine compounds (U.S. Pat. No. 5,767,158), rutin (U.S. Pat. No. 5,145,782), escinol (U.S. Pat. No. 5,728,683), salicylic acids (U.S. Pat. No. 5,700, 784), angiogenin (U.S. Pat. No. 5,698,185), mercaptodextran (U.S. Pat. No. 6,077,503), ellagic acid (U.S. Pat. No. 6,066, 312), phosphinic acids (U.S. Pat. No. 6,280,715), boron containing compounds (U.S. Pat. No. 5,993,835), plant extracts (from Pueraria, U.S. Pat. No. 6,352,685; Moms, U.S. Pat. Nos. 6,197,304; 6,066,312; and 5,872,254; acerola cherry fermentate, U.S. Pat. No. 5,747,006; furanones, U.S. Pat. No. 5,602,256; and others, U.S. Pat. No. 5,773,014).

Diarylalkanes are a rare class of natural product. To date, there are more than 179,000 natural compounds listed in *the*

*Dictionary of Natural Products* on CD-ROM (Chapman & Hall/CRC, Version 12:2 Jan. 2004), of which only 82 are diarylpropanes (n=3). *Broussonetia papyrifera* is a deciduous tree in Moracea family and more than twenty diarylpropanes have been isolated from this genera alone (Keto et al. (1986) Chem. Pharm. Bull. 34:2448; Ikuta et al. (1986) Chem. Pharm. Bull. 34:1968; Takasugi et al. (1984) Chem. Lett. 689; Gonzalez et al. (1993) Phytochem. 32:433). Bioassay directed fractionation of an extract of *Broussonetia papyrifera* yielded four diarylpropanes which did not have aromatase inhibitory activity. (Lee et al. (2001) J. Nat. Prod. 64:1286). However, two prenylated diarylpropanes isolated from the same plant exhibited cytotoxicity against several cancer cell lines (Ko et al. (1999) J. Nat. Prod. 62:164) and broussonin A exhibited anti-fungal activity (Iida et al. (1999) Yakugaku Zasshi. 119:964).

A number of diarylalkanes have also been isolated from the *Iryanthera* species (Myristicaceae). (Alyea et al. (1975) Phytochem. 14:2832; de Almeida et al. (1979) Phytochem. 18:1015; Braz et al. (1980) Phytochem. 19:1195; Diaz et al. (1986) Phytochem. 25:2395). Four dihydrochalcones isolated from *Iryanthera lancifolia* showed antioxidant activity (Silva et al. (1999) J. Nat. Prod. 62:1475). A number diarylpropanes have also been were isolated from the *Virola* species of Myristicaceae. (Braz et al. (1976) Phytochem. 15:567; Hagos et al. (1987) Plant Med. 53:57; Gonzalez et al. (1993) Phytochem. 32:433; Kijjoa et al. (1981) Phytochem. 20:1385; Talukdar et al. (2000) Phytochem. 53:155).

Other diarylpropanes isolated from natural sources include those from *Pterocarpus marsupium* (Fabaceae) (Rao et al. (1984) Phytochem. 23:897; Maurya et al. (1985) J. Nat. Prod. 48:313), *Lindera umbellate* (Lauraceae) (Morimoto et al. (1985) Chem. Pharm. Bull. 33:2281), *Helichrysum mundii* (Compositae) (Bohlmann et al. (1978) Phytochem. 17:1935), *Viscum angulatum* (Loranthaceae) (Lin et al. (2002) J. Nat. Prod. 65:638), those from *Acacia tortilis* (Leguminosae), which have a smooth muscle relaxing effect (Hagos et al. (1987) Planta Med. 53:27), *Xanthocercis zambesiaca* (Leguminosae) (Bezuidenhout et al. (1988) Phytochem. 27:2329), and cytotoxic compounds from *Knema glomerate* (Myristicaceae) (Zeng et al. (1994) J. Nat. Prod. 57:376).

Japanese Patent No. JP05213729A teaches the use of synthetic dihydrochalcones as melanin inhibitors for treatment of skin inflammation, stains, freckles and chromatosis resulting from sun-burn. The claimed compounds have the following general formula:

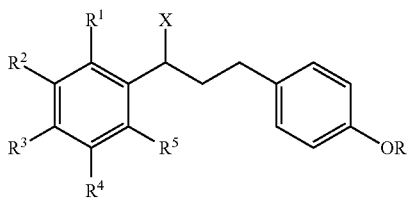

wherein X is selected from H, OH or =O; R is H or Me; and $R^1$-$R^5$ are independently selected from H, OR and $NH_2$. Thus, the disclosed dihydrochalcones contain a single hydroxy/methoxy substituent on one phenyl ring and five non-specific substituents ($R^1$-$R^5$) on the second ring. No enzyme inhibition for any of the claimed compositions was measured, rather the inhibition of melanin was determined by measurement of the amount of melanin produced by cultured skin cells and color changes of animal skin following UV stimulation. In the current invention, one of the compounds disclosed in JP05213729A, 144-hydroxyphenyl)-3-(4'-hydroxyphenyl)-1-propanol, was synthesized and its ability to inhibit tyrosinase was measured. This compound exhibited only moderate inhibition of tyrosinase ($IC_{50}$=305 μM, Table 2.) The present invention teaches novel diarylalkanes which have a unique substitution pattern wherein at least one of the two aromatic rings $Ar_1$ or $Ar_2$ are substituted with 1-5 R' groups ($R'_1$-$R'_5$) and wherein at least 2 of said of $R'_1$-$R'_5$ are not H). These compounds exhibit an unexpected ability to inhibit the activity of tyrosinase, which is 4-600 fold greater than the compounds taught by JP05213729. It is believed that to date there are no published reports any of the compounds taught in the instant application.

SUMMARY OF THE INVENTION

The present invention includes a method for inhibiting the activity of an enzyme with a binuclear active site, referred to herein as a binuclear enzyme, said method comprising administering to a host in need thereof an effective amount of one or more diarylalkane(s), wherein said diarylalkanes are synthesized and/or isolated from a one or more plants. Examples of binuclear enzymes included within the scope of the present invention include, but are not limited to tyrosinase, arginase, urease, cytochrome c oxidase, proton pumping heme-copper oxidase, bifunctional carbon monoxide dehydrogenase/acetyl-coenzyme A synthase, ribonucleotide reductase, metalo-beta-lactamase, H(+)-ATPase and alternative oxidase, and bacterial phosphotriesterase. In one embodiment, the binuclear enzyme is tyrosinase.

The present invention also includes a method for the prevention and treatment of diseases and conditions related to the activity of binuclear enzymes. The method of prevention and treatment according to this invention comprises administering internally or topically to a host in need thereof a therapeutically effective amount of one or more diarylalkane(s). Depending on the binuclear enzyme being inhibited the diarylalkane may be used as an anti-microbial, anti-fungal, anti-malaria, or anti-viral agent, a regulator for the production of nitric oxide as a means of controlling male and female sexual arousal, an anti-inflammatory drug, an antioxidant, a regulator of drug metabolism and an inhibitor or the growth of cancers and solid tumors. The diarylalkane may also be used in the prevention and treatment of periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plague and calculus, tooth decalcification, proteolysis and caries (decay).

The present invention further includes methods for the prevention and treatment of diseases and conditions related to the overproduction or uneven distribution of melanin, said method comprising administering internally or topically to a host in need thereof a therapeutically effective amount of one or more diarylalkane(s). Diseases and conditions related to the overproduction or uneven distribution of melanin include, but not limited to suntan, hyper pigmentation spots caused by skin aging, liver diseases, thermal burns and topical wounds, skin pigmentation due to inflammatory conditions caused by fungal, microbial and viral infections, vitilago, carcinoma, melanoma, as well as other mammalian skin conditions.

The method can also be used for preventing and treating skin darkening and damage resulting from exposure to ultraviolet (UV) radiation, chemicals, heat, wind and dry environments. Finally, the method can be used for preventing and treating wrinkles, saggy skin, lines and dark circles around the eyes, soothing sensitive skin and preventing and treating dermatitis and other allergy related conditions of the skin. In addition to their use for the prevention and treatment of the above described diseases and conditions of the skin, the therapeutic compositions described herein provide an efficacious composition that yields the benefit of smooth and youthful skin appearance with improved skin color, enhanced elasticity, reduced and delayed aging, enhanced youthful appearance and texture, and increased flexibility, firmness, smoothness and suppleness.

By chelating with metal ions diarylalkanes also can be used to deliver essential metal ions into the blood stream of the host, and/or carry metal ions through the skin or blood/brain barrier, as well as, other membranes. In this embodiment, the method comprises administering to a host in need thereof a therapeutically effective amount of one or more diarylalkane(s), together with the metal ion(s) to be delivered. In this capacity the diarylalkanes can be used to treat diseases and conditions including, but not limited to anemia and other iron deficiencies, inflammation; obesity and diabetes mellitus, periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plague and calculus, tooth decalcification, proteolysis and caries (decay), viral infections insomnia, suppressed immune function, osteoporosis, amenorrhea, dysmenorrheal, epilepsy, hypertension, cholesterolemea, coronary and cerebral vasospasms, diarrhea, Parkinson's disease, Alzheimer's disease, cancers, rheumatoid arthritis, male infertility and macular degeneration. The metal ions are selected from the group including, but not limited to copper, chromium, iron, zinc, boron, lithium, selenium, calcium, manganese, magnesium molybdenum and other metal ions.

In yet another embodiment, the dialkylalkanes and dialkyl alkanols can be used in the food industry to prevent browning and color changes in fruits, mushrooms and other food products.

The present invention also includes a novel composition of matter comprised of one or more diarylalkanes, wherein said diarylalkanes are selected from the group of compounds represented by the following general structure:

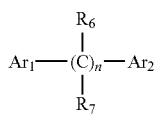

wherein $Ar_1$ and $Ar_2$ are independently selected from the group consisting of a substituted 5- or 6-membered aromatic or heteroaromatic ring, wherein each 6-membered aromatic or heteroaromatic ring is independently substituted with 1-5 R' groups ($R'_1$-$R'_5$), and each 5-membered aromatic or heteroaromatic ring is substituted with 1-4 R' groups ($R'_1$-$R'_4$), except when $Ar_1$ and $Ar_2$ are both a 6-membered aromatic ring, i.e. a phenyl group at least one of $Ar_1$ and $Ar_2$ are substituted with 1-5 R' groups ($R'_1$-$R'_5$), wherein at least 2 of said of $R'_1$-$R'_5$ are not H wherein R' independently selected from the group consisting of —H, —OH, —SH, —OR, —CN, —SR, —NH$_2$, —NHR, —NR$_2$, X, and a glycoside of a monosaccharide or oligosaccharide comprised of 2-6 monosaccharides, wherein said monosaccharide(s) are independently selected from the group consisting of an aldopentose, methyl-aldopentose, aldohexose, ketohexose and chemical derivatives thereof; wherein R is an alkyl group having between 1-20 carbon atoms and X is a halogen, selected from the group consisting of Cl, Br, F, I;

$R_6$, and $R_7$ are independently selected from the group consisting of —H, —OH, —OR, —CN, —NHR, —NH$_2$ and —X, wherein R is an alkyl group having between 1-20 carbon atoms and wherein X is a halogen, selected from the group consisting of Cl, Br, F, I; and n=1 to 10. In a preferred embodiment n=2-4.

The In one embodiment, said diarylalkanes are selected from the group of compounds represented by the following general structure:

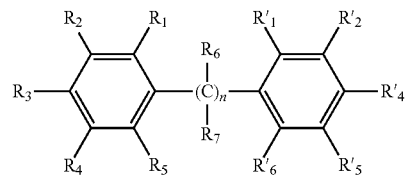

wherein $R_1$, $R_2$, $R_3$, $R_4$, $R_5$ $R'_1$, $R'_2$, $R'_3$, $R'_4$, and $R'_5$ are independently selected from the group consisting of —H, —OH, —SH, —OR, —CN, —SR, —NH$_2$, —NHR, —NR$_2$, X, and a glycoside of a monosaccharide or oligosaccharide comprised of 2-6 monosaccharides, wherein said monosaccharide(s) are independently selected from the group consisting of an aldopentose, methyl-aldopentose, aldohexose, ketohexose and chemical derivatives thereof; wherein R is an alkyl group having between 1-20 carbon atoms and X is a halogen, selected from the group consisting of Cl, Br, F, I, and wherein at least 2 of $R_1$-$R_5$ or at least 2 of $R'_1$-$R'_5$ are not H;

$R_6$, and $R_7$ are independently selected from the group consisting of —H, —OH, —OR, —CN, —NHR, —NH$_2$ and —X, wherein R is an alkyl group having between 1-20 carbon atoms and wherein X is a halogen, selected from the group consisting of Cl, Br, F, I; and n=1 to 10. In a preferred embodiment n=2-4.

In one embodiment, the diarylalkanes of this invention are isolated from one or more plants selected from the family of plants including, but not limited to Compositae, Fabaceae, Lauraceae, Leguminosae, Liliaceae, Loranthaceae, Moracea, and Myristicaceae families. The diarylalkanes of this invention can also be extracted, concentrated, and purified from the genera of high plants, including but not limited to *Acacia, Broussonetia, Dianella, Helichrysum, Iryanthera, Knema, Lindera, Pterocarpus, Viscum,* and *Xanthocercis*. The diarylalkanes can be found in different parts of plants, including but not limited to stems, stem barks, heart woods, trunks, trunk barks, twigs, tubers, roots, root barks, young shoots, seeds, rhizomes, flowers and other reproductive organs, leaves and other aerial parts. In a preferred embodiment, the diarylalkanes are isolated from a plant or plants in the Broussonetia, Dianella, and *Iryanthera* genus.

In another embodiment, the diarylalkanes of this invention are obtained by synthetic methods. Included in this invention is a method of synthesizing diarylalkanes and diarylalkanols said method comprising reducing a compound having the following general structure:

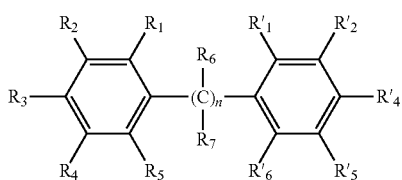

wherein $R_1$-$R_5$ and $R'_1$-$R'_5$ and n are as defined above and wherein $R_6$ and $R_7$ together form one or more carbonyl group(s). The reducing agent can be selected from any known reducing agent for the reduction of ketones to alcohols including, but not limited to borohydrides, $H_2$ in the presence of a catalyst, NaH and $LiAlH_4$. In one embodiment the reducing agent is $NaBH_4$.

In yet another embodiment, the diarylalkanes are obtained by synthetic modification of a naturally occurring compound isolated from a plant source. For example, the naturally occurring compound butein is isolated from a plant source, dehydrated and reduced to yield the corresponding diarylalkanol.

In yet another embodiment, the diarylalkanes are obtained by the reaction of two appropriately substituted aromatic compounds. Feasible chemical reactions for synthesizing these compounds from two substituted aromatic compounds include, but are not limited to Aldol condensation between a substituted benzaldehyde and a substituted acetophenone; Claisen-Schmidt reaction or crossed aldol condensation between an aldehyde and a ketone; Grignard reaction using an organomagnesium halide of one substituted aromatic ring to link the second substituted aromatic ring through addition reaction to the carbonyl group on the molecule; Claisen rearrangement by an intra-molecular isomerization, in which an esterified phenol with appropriate substitution groups will be isomerized to link the second aromatic rings at the ortho-position of the phenol followed by a reducing reaction; and a Suzuki coupling reaction, in which two substituted aromatic rings are converted to arylboronic acids and then linked by an alkyl halide by using a carefully selected palladium catalyst. These reactions are well known to those of skill in the art and the conditions for such reactions can be determined using the information disclosed herein for the synthesis of these compounds.

The present invention implements a strategy that combines an inhibition assay with a chemical dereplication process to identify active plant extracts and the particular compounds within those extracts that specifically inhibit binuclear enzymes. This approach involves a combination of natural product isolation, organic synthesis, molecular modeling and enzymatic inhibition assays to optimize the structure and maximize effectiveness of the drug. This method is described in U.S. application Ser. No. 10/185,758, filed Jun. 27, 2002, entitled "Method for Generating, Screening and Dereplicating Natural Product Libraries for the Discovery of Therapeutic Agents," which is incorporated herein by reference in its entirety. The efficacy of this method is demonstrated using a tyrosinase inhibition assay as described in the Example section below. The purity of the diarylalkanes evaluated according to the method of this invention is in the range of 0.01% to 100%, depending on the methodology used to obtain the compound(s).

In a preferred embodiment, the dose of the diarylalkane administered to the host in need thereof is an efficacious, nontoxic quantity generally selected from the range of 0.001% to 100% based on total weight of the final formulation, and/or 0.01 mg to 200 mg per kilogram based on the body weight of the host. Persons skilled in the art using routine clinical testing are able to determine optimum doses for the particular ailment being treated. The present invention provides commercially viable options for the synthesis, and/or isolation, purification and formulation of diarylalkanes to yield composition of matter having desirable physiological activity. The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a pure or a mixture of diarylalkanes synthesized and/or isolated from a single plant or multiple plants. In a preferred embodiment the composition is administered topically.

It is to be understood that both the foregoing general description and the following detailed description are exemplary and explanatory only and are not restrictive of the invention as claimed.

BRIEF DESCRIPTION OF THE DRAWINGS

FIGS. 3A and 3B depict the structure, name, mechanism of action, and other effects of known tyrosinase inhibitors.

DETAILED DESCRIPTION OF THE PREFERRED EMBODIMENT

Figure 1:
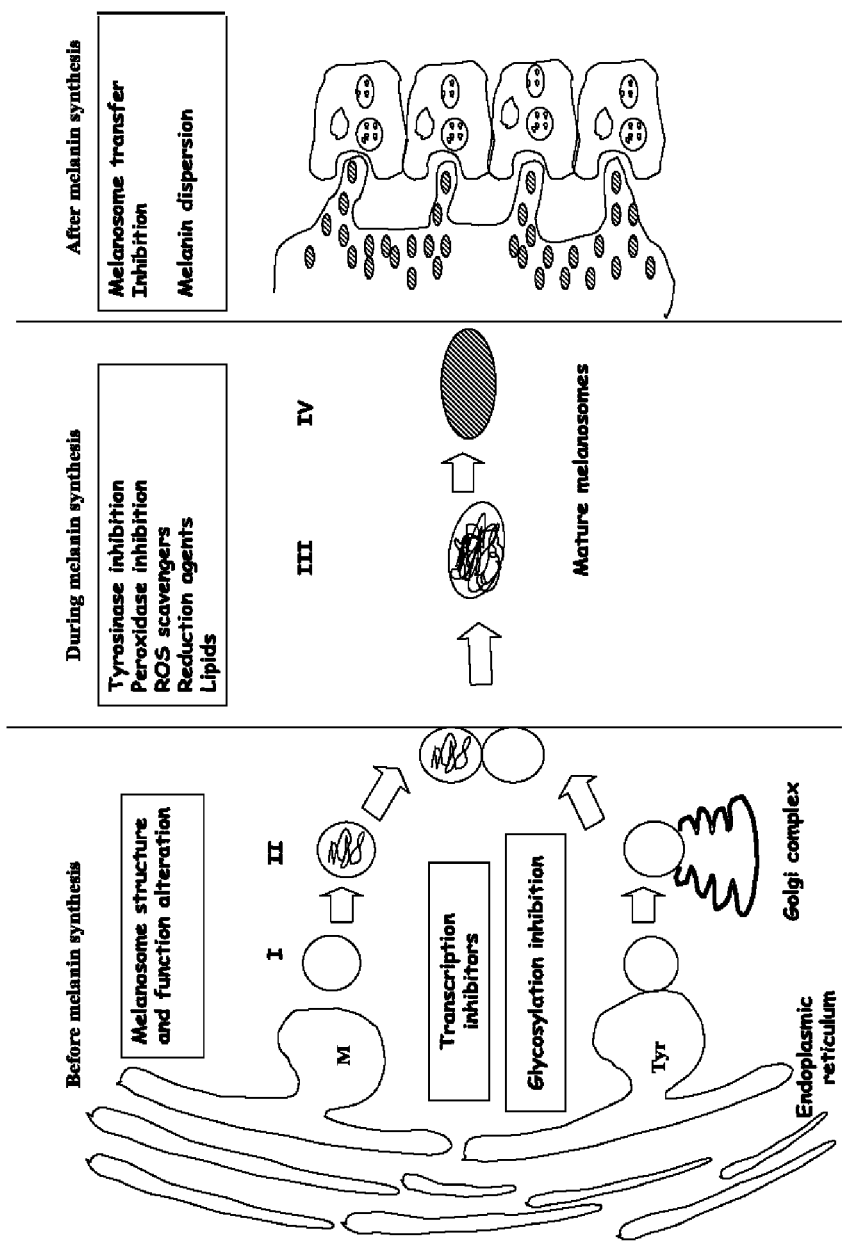
FIG. 1 illustrates the process of melanogenesis, together with various potential mechanisms for regulating this process.
Figure 2:
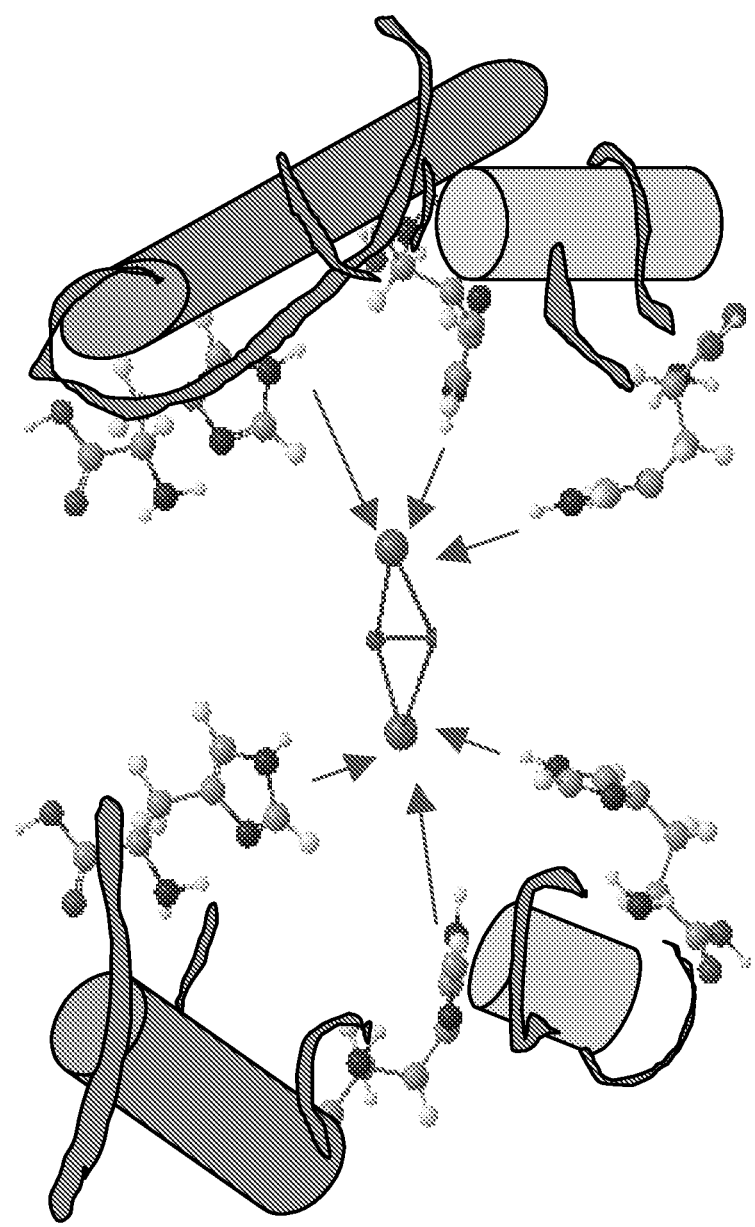
FIG. 2 illustrates the structure of the active site of tyrosinase. As can be seen in this figure, two copper ions are closely spaced and each is coordinated to three histidines through the N-E nitrogen atom of its side chain.

The present invention relates generally to the prevention and treatment of diseases and conditions mediated by binuclear enzymes. Specifically, the present invention includes a method for inhibiting the activity of an enzyme having a binuclear active site. Included in the present invention are novel compositions comprised of one or more diarylalkane(s). The diarylalkanes of the present invention can be isolated from one or more plant sources or can be obtained by organic synthesis. Further included in the present invention are methods for isolating these compounds from a natural source and methods for synthesizing these compounds. In one embodiment, the diarylalkanes are obtained by synthetic modification of a naturally occurring compound isolated from a plant source.

Various terms are used herein to refer to aspects of the present invention. To aid in the clarification of the description of the components of this invention, the following definitions are provided. Unless defined otherwise all technical and scientific terms used herein have the meaning commonly understood by one of ordinary skill in the art to which this invention belongs.

It is to be noted that as used herein the term "a" or "an" entity refers to one or more of that entity; for example, a diarylalkane refers to one or more diarylalkanes. As such, the terms "a" or "an", "one or more" and "at least one" are used interchangeably herein.

"Diarylalkanes" as used herein are a specific class of aromatic compounds having the following general structure: The present invention also includes a novel composition of matter comprised of one or more diarylalkanes, wherein said diarylalkanes are selected from the group of compounds represented by the following general structure:

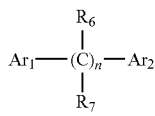

wherein $Ar_1$ and $Ar_2$ are independently selected from the group consisting of a substituted 5- or 6-membered aromatic or heteroaromatic ring, wherein each 6-membered aromatic or heteroaromatic ring is independently substituted with 1-5 R' groups ($R'_1$-$R'_5$), and each 5-membered aromatic or heteroaromatic ring is substituted with 1-4 R' groups ($R'_1$-$R'_4$), except when $Ar_1$ and $Ar_2$ are both a 6-membered aromatic ring, i.e. a phenyl group at least one of $Ar_1$ and $Ar_2$ are substituted with 1-5 R' groups ($R'_1$-$R'_5$), wherein at least 2 of said of $R'_1$-$R'_5$ are not H wherein R' is independently selected from the group consisting of —H, —OH, —SH, —OR, —CN, —SR, —NH$_2$, —NHR, —NR$_2$ and X, and a glycoside of a monosaccharide or oligosaccharide comprised of 2-6 monosaccharides, wherein said monosaccharide(s) are independently selected from the group consisting of an aldopentose, methyl-aldopentose, aldohexose, ketohexose and chemical derivatives thereof; wherein R is an alkyl group having between 1-20 carbon atoms and X is a halogen, selected from the group consisting of Cl, Br, F and I;

$R_6$, and $R_7$ are independently selected from the group consisting of —H, —OH, —OR, —CN, —NHR, —NH$_2$, and —X, wherein R is an alkyl group having between 1-20 carbon atoms and wherein X is a halogen, selected from the group consisting of Cl, Br, F, I; and n=1 to 10. In a preferred embodiment n=2-4.

In one embodiment, said diarylalkanes and diarylalkanols are selected from the group of compounds represented by the following general structure:

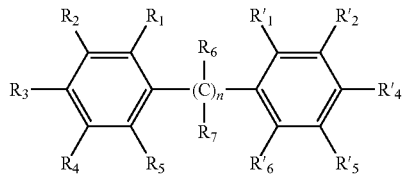

wherein $R_1$, $R_2$, $R_3$, $R_4$, $R_5$ $R'_1$, $R'_2$, $R'_3$, $R'_4$, and $R'_5$ are independently selected from the group consisting of —H, —OH, —SH, —OR, —CN, —SR, —NH$_2$, —NHR, —NR$_2$, X, and a glycoside of a monosaccharide or oligosaccharide comprised of 2-6 monosaccharides, wherein said monosaccharide(s) are independently selected from the group consisting of an aldopentose, methyl-aldopentose, aldohexose, ketohexose and chemical derivatives thereof; wherein R is an alkyl group having between 1-20 carbon atoms and X is a halogen, selected from the group consisting of Cl, Br, F, I, and wherein at least 2 of $R_1$-$R_5$ or at least 2 of $R'_1$-$R'_5$ are not H;

$R_6$, and $R_7$ are independently selected from the group consisting of —H, —OH, —OR, —CN, —NHR, —NH$_2$, and —X, wherein R is an alkyl group having between 1-20 carbon atoms and wherein X is a halogen, selected from the group consisting of Cl, Br, F and I; and n=1 to 10. In a preferred embodiment n=2-4.

"Diarylalkanols" as used herein are a specific type of "diarylalkanes" having at least one hydroxyl group ($R_6$ and/or $R_7$=—OH) attached to the alkyl carbons between the two aromatic rings.

"Binuclear enzyme" as used herein refers to an enzyme which has a binuclear active site, an example of which is tyrosinase which has two copper ions at its active site as discussed above. Binuclear enzymes include, but are not limited to tyrosinase, arginase, urease, cytochrome c oxidase, proton pumping heme-copper oxidase, bifunctional carbon monoxide dehydrogenase/acetyl-coenzyme A synthase, ribonucleotide reductase, metalo-beta-lactamase, H(+)-ATPase and alternative oxidase, and bacterial phosphotriesterase.

"Therapeutic" as used herein, includes prevention, treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

"Placebo" refers to the substitution of the pharmaceutically or therapeutically effective dose or amount dose sufficient to induce a desired biological that may alleviate the signs, symptoms or causes of a disease with a non-active substance.

A "host" or "patient" or "subject" is a living mammal, human or animal, for whom therapy is desired. The "host," "patient" or "subject" generally refers to the recipient of the therapy to be practiced according to the method of the invention. It should be noted that the invention described herein may be used for veterinary as well as human applications and that the term "host" should not be construed in a limiting manner. In the case of veterinary applications, the dosage ranges can be determined as described below, taking into account the body weight of the animal.

As used herein a "pharmaceutically acceptable carrier" refers to any carrier, which does not interfere with effectiveness of the biological activity of the active ingredient and which is not toxic to the host to which it is administered. Examples of "pharmaceutically acceptable carriers" include, but are not limited to, any of the standard pharmaceutical carriers such as a saline solution, i.e. Ringer's solution, a buffered saline solution, water, a dextrose solution, serum albumin, and other excipients and preservatives for tableting and capsulating formulations.

The present invention includes a method for inhibiting the activity of an enzyme with a binuclear active site, referred to herein as a binuclear enzyme, said method comprising administering to a host in need thereof an effective amount of one or more diarylalkane(s), wherein said diarylalkanes are synthesized and/or isolated from a one or more plants. Examples of binuclear enzymes included within the scope of the present invention include, but are not limited to tyrosinase, arginase, urease, cytochrome c oxidase, proton pumping heme-copper oxidase, bifunctional carbon monoxide dehydrogenase/acetyl-coenzyme A synthase, ribonucleotide reductase, metalo-beta-lactamase, H(+)-ATPase and alternative oxidase, and bacterial phosphotriesterase. In one embodiment, the binuclear enzyme is tyrosinase.

The present invention also includes a method for the prevention and treatment of diseases and conditions related to the activity of binuclear enzymes. The method of prevention and treatment according to this invention comprises administering internally or topically to a host in need thereof a therapeutically effective amount of one or more diarylalkane(s). Depending on the binuclear enzyme being inhibited the diarylalkane may be used as an anti-microbial, anti-fungal, anti-malaria, or anti-viral agent, a regulator for the production of nitric oxide as a means of controlling male and female sexual arousal, an anti-inflammatory drug, an antioxidant, a regulator of drug metabolism, for treatment and prevention of periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plaque and calculus, tooth decalcification, proteolysis and caries (decay). and an inhibitor of the growth of cancers and solid tumors.

The present invention further includes methods for the prevention and treatment of diseases and conditions related to the overproduction or uneven distribution of melanin, said method comprising administering internally or topically to a host in need thereof a therapeutically effective amount of one or more diarylalkane(s). Diseases and conditions related to the overproduction or uneven distribution of melanin include, but not limited to suntan, hyper pigmentation spots caused by skin aging, liver diseases, thermal burns and topical wounds, skin pigmentation due to inflammatory conditions caused by fungal, microbial and viral infections, vitilago, carcinoma, melanoma, as well as other mammalian skin conditions.

The method can also be used for preventing and treating skin darkening and damage resulting from exposure to ultraviolet (UV) radiation, chemicals, heat, wind and dry environments. Finally, the method can be used for preventing and treating wrinkles, saggy skin, lines and dark circles around the eyes, soothing sensitive skin and preventing and treating dermatitis and other allergy related conditions of the skin. In addition to their use for the prevention and treatment of the above described diseases and conditions of the skin, the therapeutic compositions described herein provide an efficacious composition that yields the benefit of smooth and youthful skin appearance with improved skin color, enhanced elasticity, reduced and delayed aging, enhanced youthful appearance and texture, and increased flexibility, firmness, smoothness and suppleness.

By chelating with metal ions diarylalkanes also can be used to deliver essential metal ions into the blood stream of the host, and/or carry metal ions through the skin or blood/brain barrier, as well as, other membranes. In this embodiment, the method comprises administering to a host in need thereof a therapeutically effective amount of one or more diarylalkane(s), together with the metal ion(s) to be delivered. In this capacity the diarylalkanes can be used to treat diseases and conditions including, but not limited to anemia and other iron deficiencies, inflammation; obesity and diabetes, periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plaque and calculus, tooth decalcification, proteolysis and caries (decay), and viral infections. The metal ions are selected from the group including, but not limited to copper, iron, zinc, selenium, magnesium and other metal ions.

In yet another embodiment, the dialkylalkanes can be used in the food industry to prevent browning and color changes in fruits, mushrooms and other food products.

The diarylalkanes that can be used in accordance with the following include compounds illustrated by the general structure set forth above. The diarylalkanes of this invention may be obtained by synthetic methods or may be isolated from one or more families of plants selected from the group including, but not limited to Compositae, Fabaceae, Lauraceae, Leguminosae, Liliaceae, Loranthaceae, Moracea, and Myristicaceae. The diarylalkanes of this invention can be extracted, concentrated, and purified from the genera of high plants, including but not limited to *Acacia, Broussonetia, Dianella, Helichrysum, Iryanthera, Knema, Lindera, Pterocarpus, Viscum*, and *Xanthocercis*. The diarylalkanes can be found in different parts of the plant, including but not limited to stems, stem barks, heart woods, trunks, trunk barks, twigs, tubers, roots, root barks, young shoots, seeds, rhizomes, flowers and other reproductive organs, leaves and other aerial parts. In a one embodiment, the diarylalkanes are isolated from a plant or plants in the *Broussonetia, Dianella*, and *Iryanthera* genera.

In another embodiment, the diarylalkanes of this invention are obtained by synthetic methods. Included in this invention is a method of synthesizing diarylalkanes and diarylalkanols said method comprising reducing a compound having the following general structure:

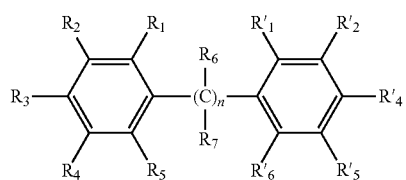

wherein

R$_1$-R$_5$ and R'$_1$-R'$_5$ and n are as defined above and wherein R$_6$ and R$_7$ together form one or more carbonyl group(s). The reducing agent can be selected from any known reducing agent for the reduction of ketones to alcohols including, but not limited to borohydrides, H$_2$ in the presence of a catalyst, NaH and LiAlH$_4$. In one embodiment the reducing agent is NaBH$_4$.

In yet another embodiment, the diarylalkanes are obtained by synthetic modification of a naturally occurring compound isolated from a plant source. For example, the naturally occurring compound butein is isolated from a plant source, dehydrated and reduced to yield the corresponding diarylalkanol.

In yet another embodiment, the diarylalkanes are obtained by the reaction of two appropriately substituted aromatic compounds. Feasible chemical reactions for synthesizing these compounds from two substituted aromatic compounds include, but are not limited to Aldol condensation between a substituted benzaldehyde and a substituted acetophenone; Claisen-Schmidt reaction or crossed aldol condensation between an aldehyde and a ketone; Grignard reaction using an organomagnesium halide of one substituted aromatic ring to link the second substituted aromatic ring through addition reaction to the carbonyl group on the molecule; Claisen rearrangement by an intra-molecular isomerization, in which an esterified phenol with appropriate substitution groups will be isomerized to link the second aromatic rings at the ortho-position of the phenol followed by a reducing reaction; and a Suzuki coupling reaction, in which two substituted aromatic rings are converted to arylboronic acids and then linked by an alkyl halide by using a carefully selected palladium catalyst. These reactions are well known to those of skill in the art and the conditions for such reactions can be determined using the information disclosed herein for the synthesis of these compounds.

Note that throughout this application various citations are provided. Each of these citations is specifically incorporated herein by reference in its entirety.

The present invention implements a strategy that combines a tyrosinase inhibition assay with a chemical dereplication process to identify active plant extracts and the particular compounds within those extracts that specifically inhibit the binuclear enzyme tyrosinase. As noted above, enzymes that inhibit tyrosinase may lead to a reduction in the production of melanin thereby effectively lightening the skin. A library of plant extracts was generated by extracting dry plant powders with an organic solvent, as described in Example 1. The tyrosinase inhibition assay was developed following a method reported by Jones et al. (2002) Pigment. Cell Res. 15:335, as described in Example 2. Using this assay, a total of 1144 plant extracts were screened for their ability to inhibit the activity of mushroom tyrosinase. This primary screen identified 20 plant extracts (1.75% hit rate) with potent tyrosinase inhibitory activity. Table 1 delineates percent inhibition of tyrosinase by four of these extracts isolated from four different genera.

In order to efficiently identify active compounds from the active plant extracts, a high throughput fractionation process was used, as described in Example 3. Briefly, the active extracts were fractionated using a high throughput purification (HTP) system. Each of the fractions was then tested for its ability to inhibit tyrosinase activity as per the primary assay described in Example 2. After dereplication, using a combination of HPLC with PDA and MS detectors coupled with a structure database search and elimination of fractions that contained known tyrosinase inhibitors, such as polyphenols and chromones, a total of seven active extracts were chosen for bioassay guided large-scale isolation and purification as described in Examples 4-6, using the extracts of *Broussonetia kazinoki* Sieb. Et Zucc (Moraceae), and *Dianella ensifolia* (L.) DC. (Liliaceae) for purposes of illustration.

Figure 4:
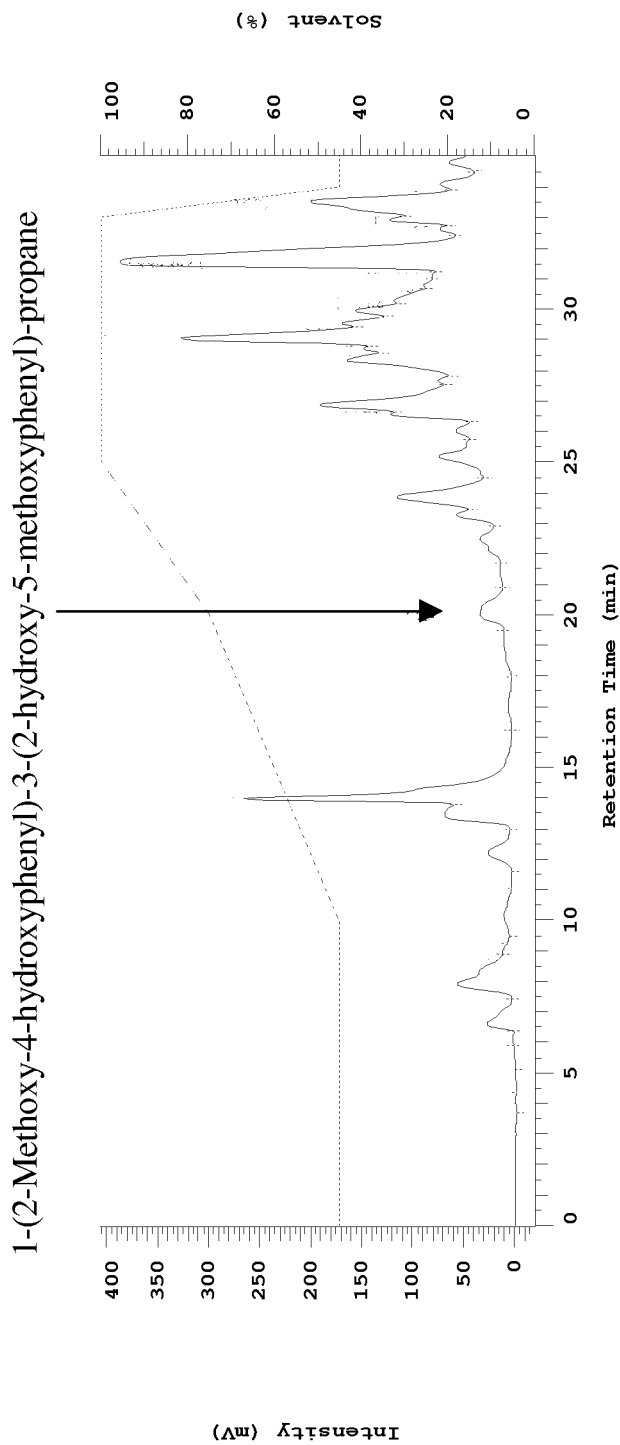
FIG. 4 illustrates the HPLC/UV chromatogram of a HTP fraction that contains the UP288 (1-(2-methoxy-4-hydroxyphenyl)-3-(2'-hydroxy-5'-methoxyphenyl)-propane) (1) as highlighted.
Figure 5:
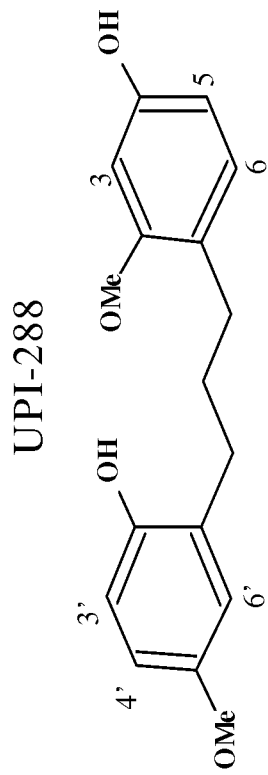
FIG. 5 depicts the chemical structure and $^{13}$C-NMR spectrum of UP288 (1).
Figure 5:
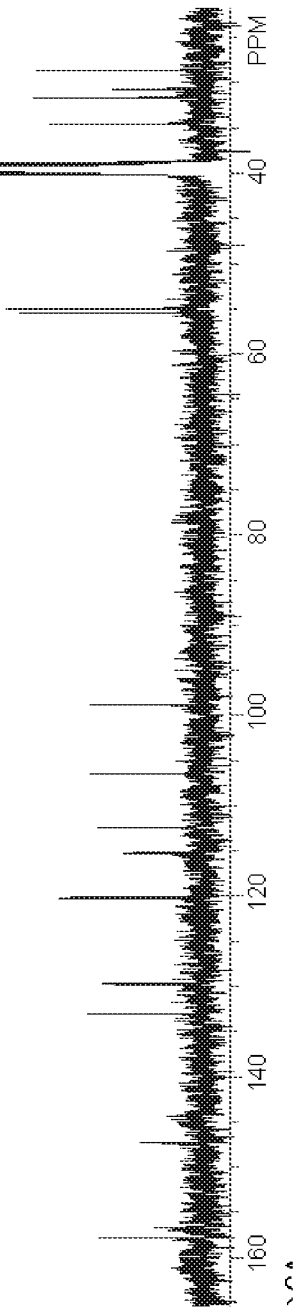
Figure 6:
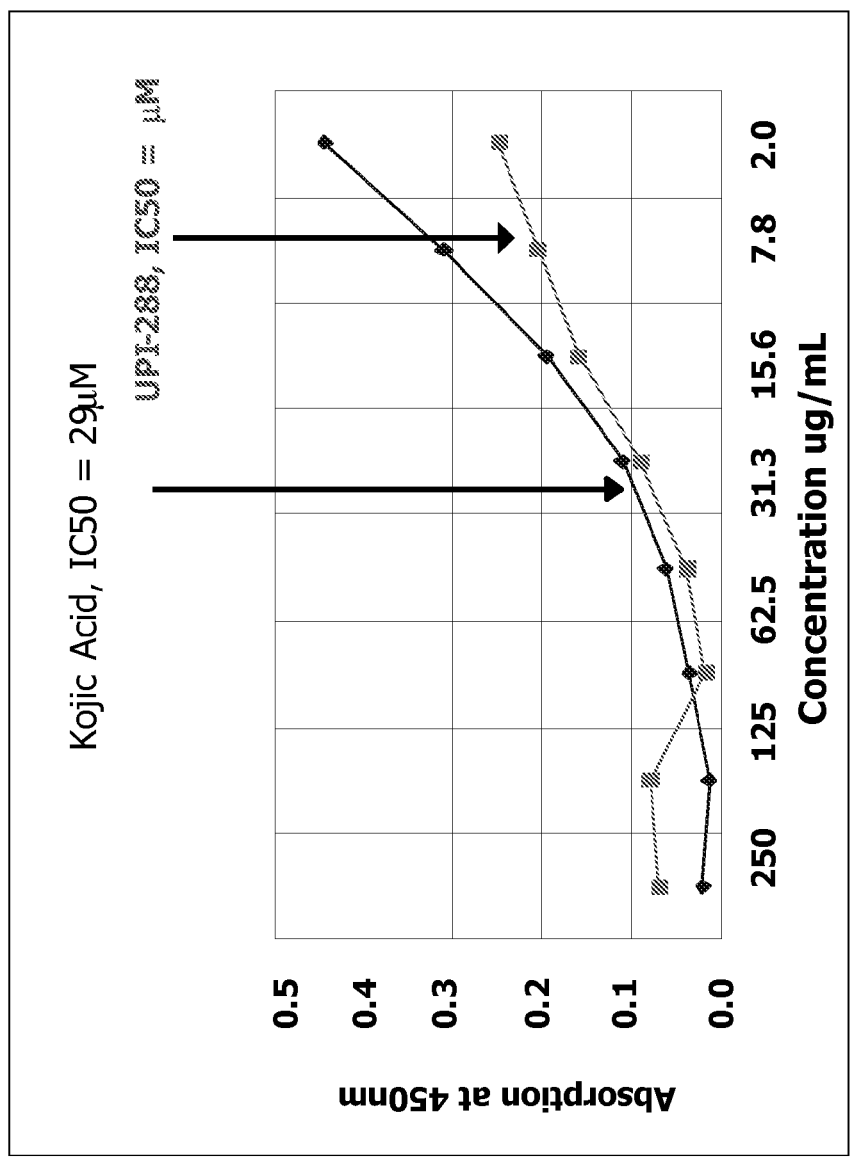
FIG. 6 illustrates tyrosinase inhibitory dose response curves and $IC_{50}$ values for UP288 and kojic acid.

Example 4 describes the extraction, separation and purification of the novel diarylpropane: 1-(2-methoxy-4-hydroxyphenyl)-3-(2'-hydroxy-5'-methoxyphenyl)-propane (UP288) (1) from *Broussonetia kazinoki* Sieb. Et Zucc (Moraceae) (whole plant) using the general method set forth in Examples 1-3. FIG. 4 illustrates the HPLC/UV chromatogram of a HTP fraction that contains the UP288. The structure of the active compound UP288 was elucidated using a combination of spectroscopic methods as set forth in Example 4. FIG. 5 depicts the chemical structure and $^{13}$C-NMR spectrum of UP288. FIG. 6 illustrates tyrosinase inhibitory dose response curves and IC$_{50}$ values for UP288 relative to kojic acid. The figure illustrates that UP288 (1) is as potent a tyrosinase inhibitor as kojic acid, having an IC$_{50}$=24 µM.

Figure 7:
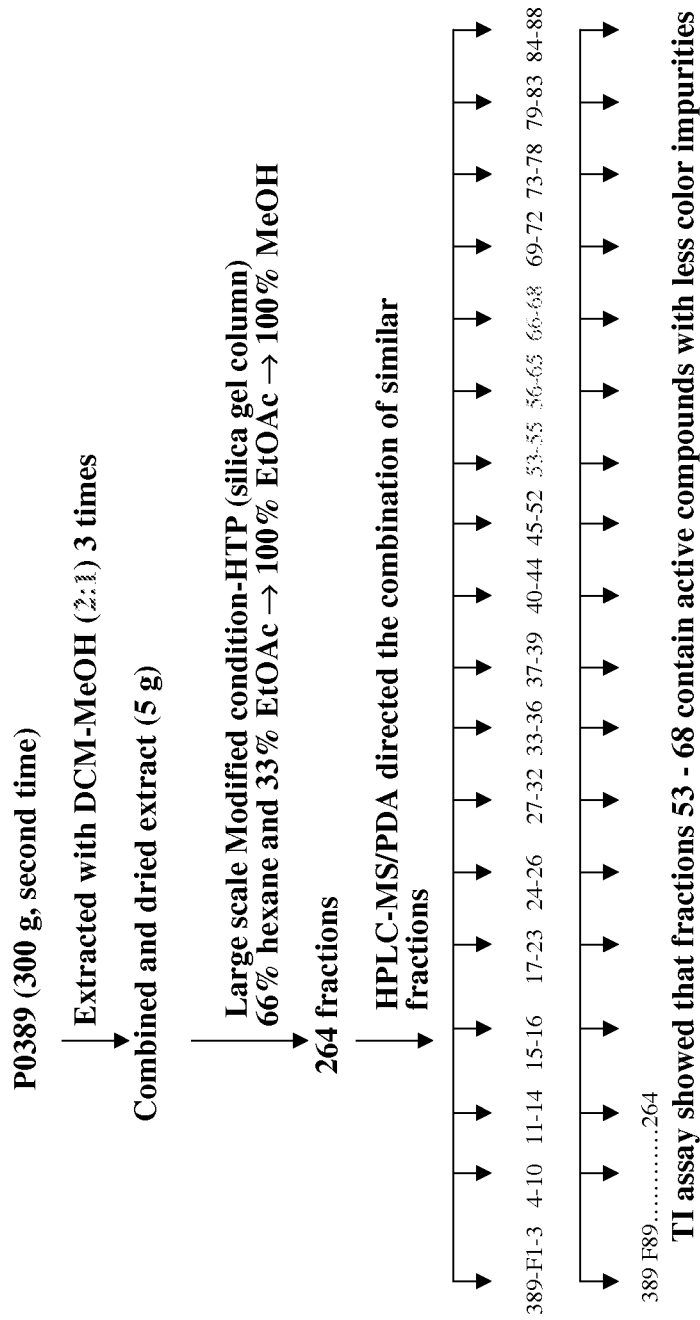
FIG. 7 depicts the bioassay-guided isolation of two active compounds (UP302a and UP302b) from *Dianella ensifolia* (P0389) (whole plant).

Surprisingly, two similar diarylalkanes were isolated and identified from a totally different family of plant—*Dianella ensifolia* (L.) DC. (Liliaceae), as described in Example 5. FIG. 7 depicts schematically the bioassay-guided isolation of these two active compounds (UP302a (2) and UP302b (3)) from *Dianella ensifolia* (P0389) (whole plant). With reference to FIG. 7, it can be seen that only fifteen column fractions from a total of 264 collected samples exhibited potent inhibition of tyrosinase. A HPLC analysis (FIG. 8) of the combined active fractions showed that active compounds were minor components in the best pool, which has already been heavily enriched. Laborious separation and purification efforts yielded two novel active compounds that have been fully characterized by NMR and other spectroscopic methods as illustrated in Example 5 and FIG. 9 as 1-(3-methyl-2,4-dimethoxyphenyl)-3-(2',4'-dihydroxyphenyl)-propane (UP302a, IC$_{50}$=0.24 µM) (2) and 1-(3-methyl-2,4-dimethoxyphenyl)-3-(2',5'-dihydroxyphenyl)-propane (IP302b, IC$_{50}$=1.2 µM) (3).

Example 6 describes the large-scale isolation of UP302a (2), the most potent tyrosinase inhibitor, isolated from *Dianella ensifolia* (DE) (whole plant). With reference to Example 6, from 4.3 kg of dried biomass, a total of 30 mg of pure UP302a (2) was obtained after multiple column fractionations on silica gel, CG-161, and C-18 resins. The structure and biological function of the isolated compound were confirmed.

Due to the low natural abundance of diarylalkanes/diarylalkanols methods to synthesize these biologically active compounds as an alternative commercial source of this class of compounds was developed. Example 7 describes a general method for the synthesis of diarylalkanes via the reduction of substituted chalcones. For purposes of illustration the reduction of 2,4-dihydroxyphenyl)-3',4'-dimethoxyphenylchalcone (4) to 1-(2,4-dihydroxyphenyl)-3-(3',4'-dimethoxyphenyl)-1-propanol (5) using sodium borohydride is described. However, as set forth in Example 7, a number of other diarylalkanes have been synthesized using this general method. All of the compounds synthesized showed high to moderate tyrosinase inhibitory activity. With respect to the general method described in Example 7, any other known reducing agents, can be used to effect this reduction, including, but are not limited to other borohydrides, H$_2$ in the presence of a catalyst, NaH and LiAlH$_4$.

Using the general reaction described in Example 7, several other substituted diarylpropanones have been converted to diarylpropanes and/or diarylpropanols as demonstrated in Examples 8, 9 and 10. Example 11 demonstrates the synthesis of a diarylpropanol using a flavonoid glycoside isolated from a natural source as the starting material.

In another embodiment, the present invention includes methods for synthesizing this class of compounds by reaction of two appropriately substituted aromatic compounds. This embodiment is illustrated in Example 12, using the reaction of resorcinol with 3-methoxy-4-hydroxycinnamic acid for purposes of illustration. Feasible chemical reactions for synthesizing these compounds from two substituted aromatic compounds include, but are not limited to Aldol condensation between a substituted benzaldehyde and a substituted acetophenone; Claisen-Schmidt reaction or crossed aldol condensation between an aldehyde and a ketone; Grignard reaction using an organomagnesium halide of one substituted aromatic ring to link the second substituted aromatic ring through addition reaction to the carbonyl group on the molecule; Claisen rearrangement by an intra-molecular isomerization, in which an esterified phenol with appropriate substitution groups will be isomerized to link the second aromatic rings at the ortho-position of the phenol followed by a reducing reaction; and a Suzuki coupling reaction, in which two substituted aromatic rings are converted to arylboronic acids and then linked by an alkyl halide by using a carefully selected palladium catalyst. These reactions are well known to those of skill in the art and the conditions for such reactions can be determined using the information disclosed herein for the synthesis of these compounds.

Example 13 sets forth the $IC_{50}$ values for a number of diarylalkanes and diarylalkanols synthesized according the methods of this invention. The compounds were evaluated using the general method described in Example 2. The $IC_{50}$ value of each sample was calculated using kinetics software to verify that the reaction was linear at a specified time and concentration. Using the methods described in Examples 7-12 a total of 24 compounds were synthesized and evaluated for their ability to inhibit tyrosinase. The results are set forth in Table 2. With reference to Table 2, it can be seen that the $IC_{50}$'s of the synthetic diarylalkanols were comparable to the naturally occurring diarylpropanes. Thus, these two classes of compounds are capable of inhibiting tyrosinase to approximately the same extent. The most active diarylalkanes and/or diarylalkanols had three carbons between the two aromatic rings. Using the calculations described in Example 17, this structural feature was demonstrated to be critical in order to generate a parallel and superimposed intra-molecular conformations. However, diarylalkanols, which contained two and four carbons between the two aromatic rings, such as 1-(2,4-dihydroxyphenyl)-2-(4'-methoxyphenyl)-1-ethanol ($IC_{50}$=77 μM) and 1,4-bis-(3,4-dihydroxyphenyl)-2,3-dimethyl-butane ($IC_{50}$=700 μM) also were able to significantly inhibit tyrosinase activity.

Using the method described in Example 2, the inhibition of tryosinase by UP302a (2) was evaluated using L-DOPA as the substrate as set forth in Example 14. The results are set forth in FIG. 10. This study revealed that UP302a (2) is a powerful competitive inhibitor having a long lasting effect. Interestingly, tyrosinase activity was not resumed for several days after incubation with UP302a. In contrast, tyrosinase activity was totally restored after only 1 hour following incubation with kojic acid. Since two of the substituents on the aromatic rings of UP302a were methoxy groups, the inhibitor cannot be easily hydroxylated and/or oxidized. This may explain both the effectiveness and duration of the inhibitory activity of UP302a. Thus, it can be concluded that these compounds will have a long lasting effect.

Figure 11:
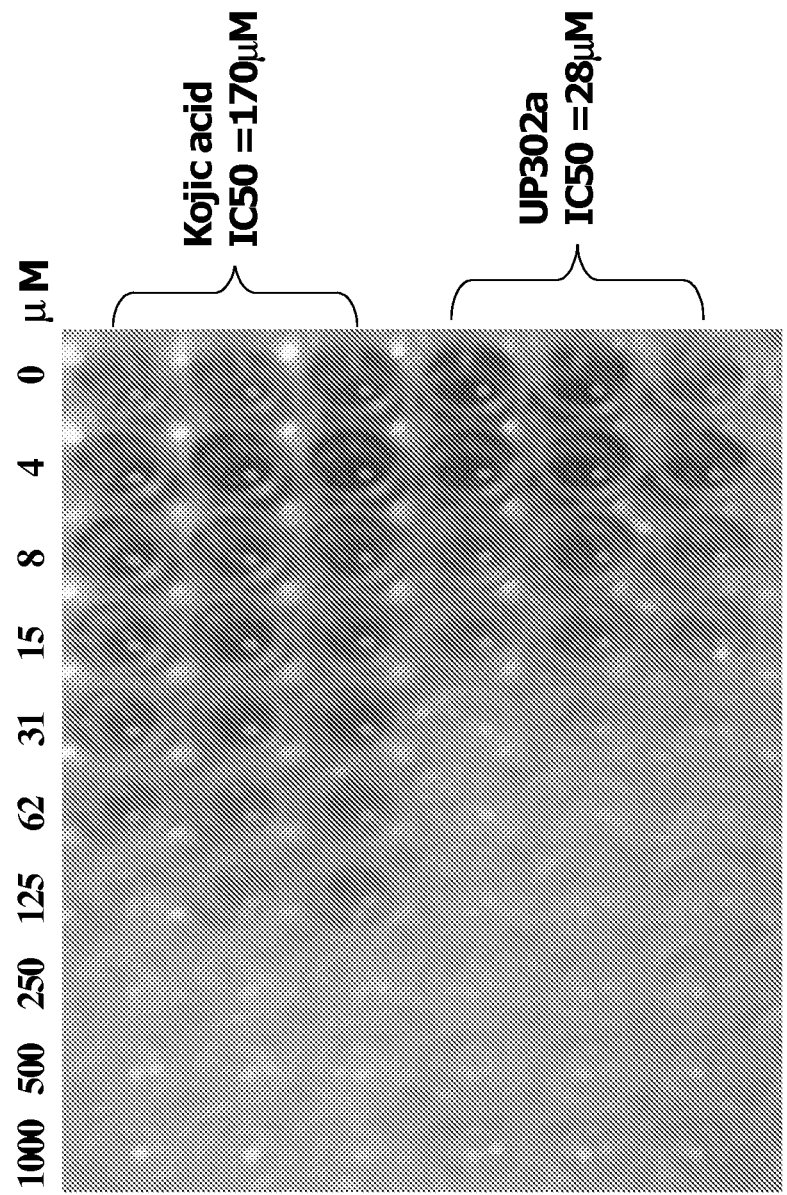
FIG. 11 illustrates the inhibition of endogenous melanin production from mouse B16 F1 cells by kojic acid and UP302a (2). Each sample was tested in triplicate at 10 different concentrations.

The efficacy of the claimed composition was also demonstrated by measuring the inhibition of melanin produced in an in vitro test on a B-16 cell line as described in Example 15. The results are set forth in FIG. 11. The reduction of endogenous melanin by UP302a (2) was almost six fold greater than that of kojic acid. Additionally, inhibition of MSH induced melanin production by UP302a was also significantly greater than kojic acid. As expected, UP288 (1) was comparable to kojic acid in the B-16 cell line model.

Example 16 describes an assay to assess the cytotoxicity of two diarylpropanes UP288 (1) and UP302a (2) relative to kojic acid. At a concentration of 250 μM, which was above $IC_{50}$ of all three tested compounds, the diarylpropanes demonstrated similar safety profiles to that of kojic acid.

Figure 12:
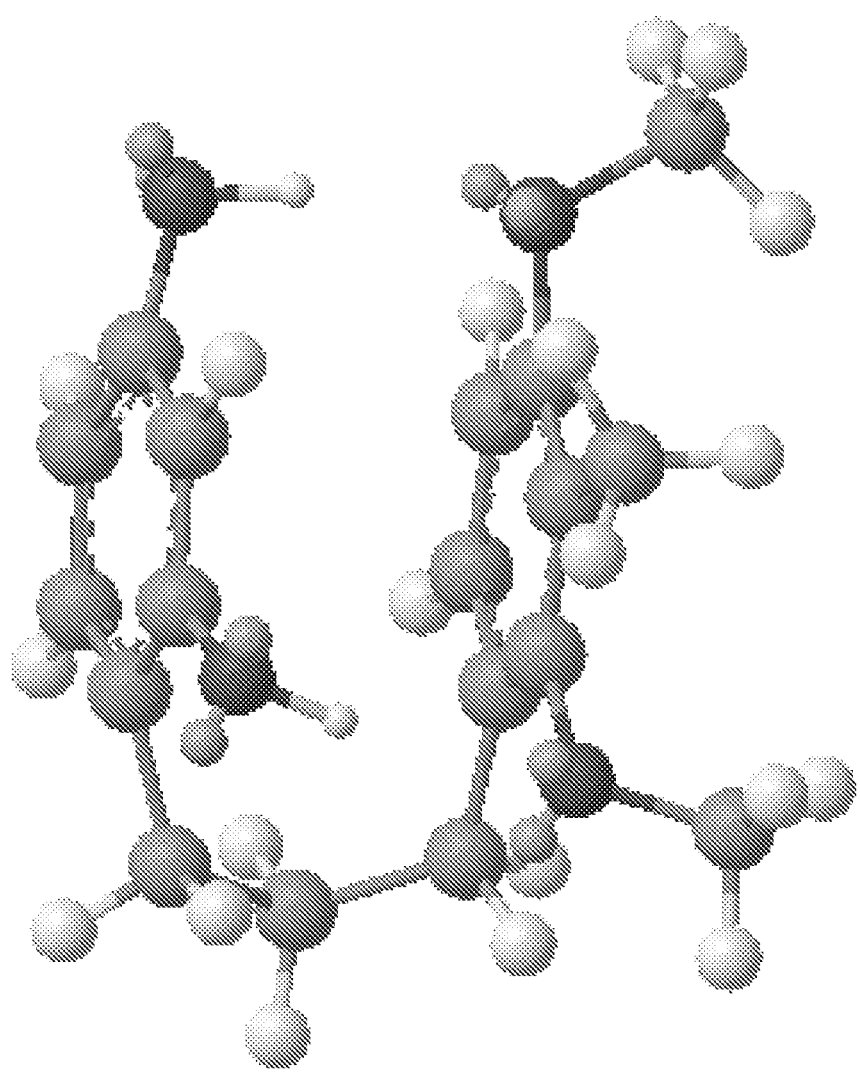
FIG. 12 depicts three-dimensional conformation of UP302a after MM2 energy minimization.
Figure 13:
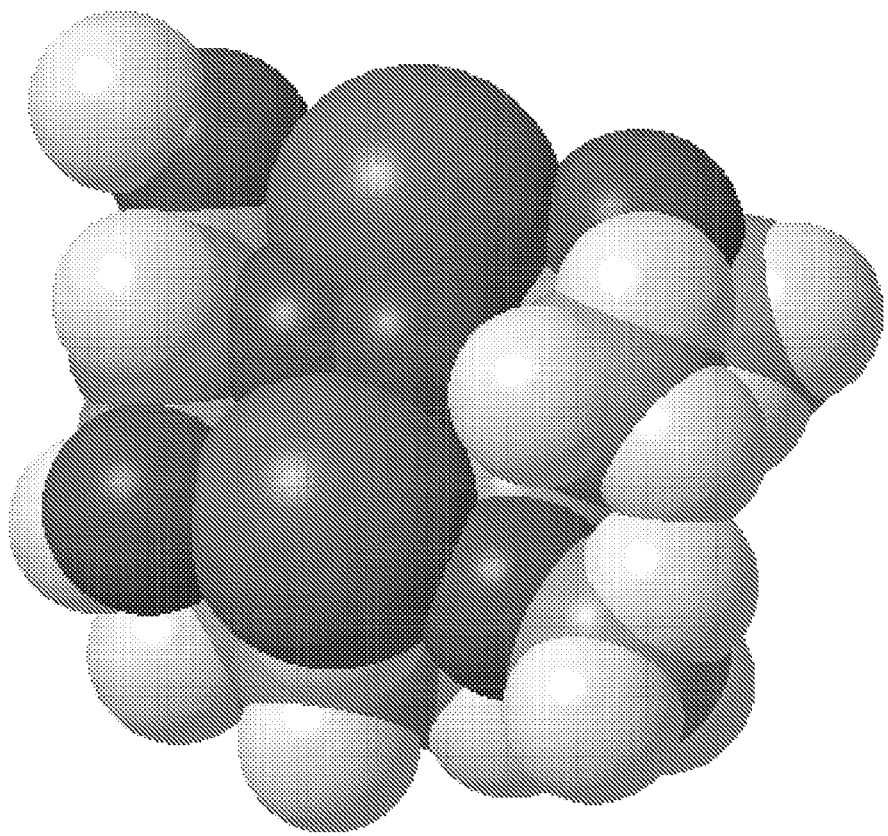
FIG. 13 illustrates the three-dimensional conformation of UP302a, when coordinated to two copper ions in the $Cu^{II}$—$O_2$—$Cu^{II}$ oxidation state.
Figure 14:
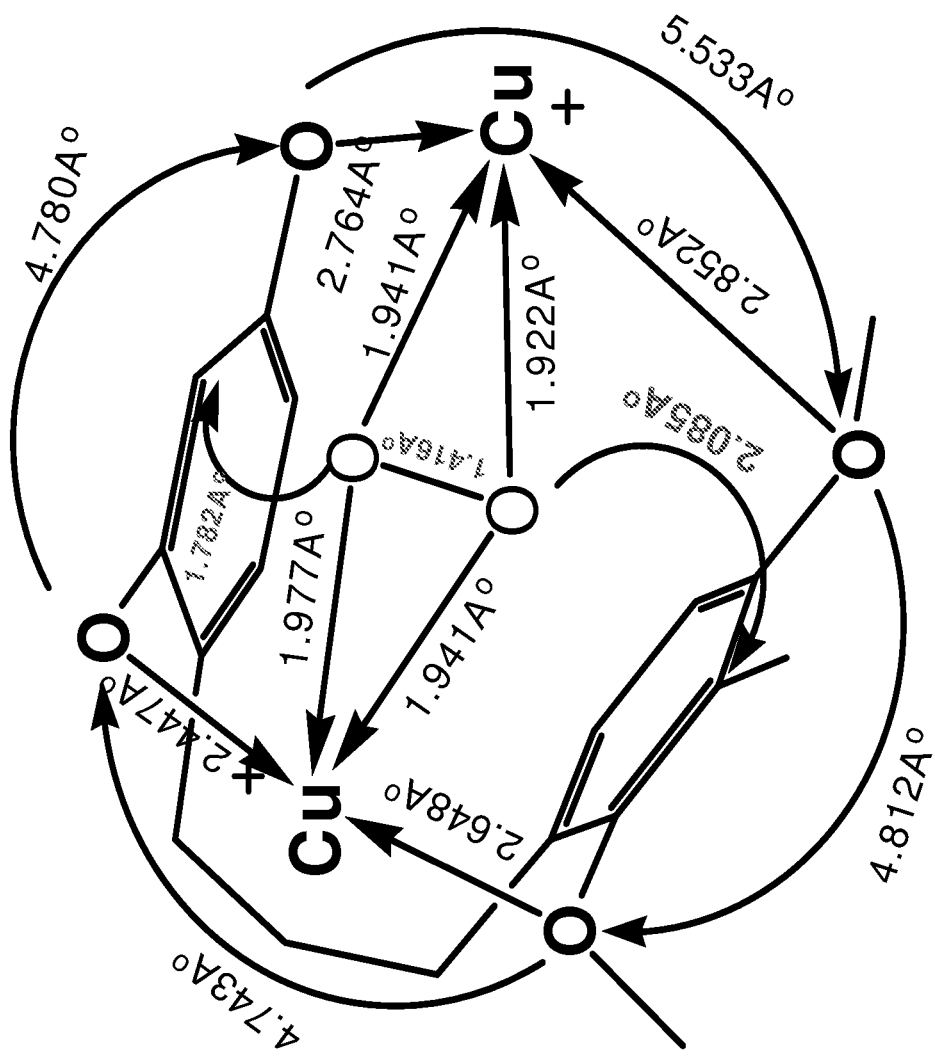
FIG. 14 depicts the distances between adjacent atoms of UP302a when chelated with copper ions in the peroxide form ($Cu^{II}$—$O_2$—$Cu^{II}$) as calculated in Example 17.

Example 17 describes the molecular modeling analyses performed to determine the most stable 3-D conformation of the active diarylalkanes and diarylalkanols. Molecular mechanics calculations were performed using Chem3D software. These calculations revealed that the most potent tyrosinase inhibitor-1-(3-methyl-2,4-dimethoxyphenyl)-3-(2',4'-dihydroxyphenyl)-propane (UP302a (2), $IC_{50}$=0.24 μM) has a very unique 3-dimentional conformation with two the aromatic rings superimposed on each other as illustrated in FIG. 12. The minimized total energy for the conformation is −4.7034 KJ/Mol and the distance between the two aromatic rings is 3.28 Å. The phenolic hydroxyl groups on the first aromatic ring are right above the two methoxy groups on the second aromatic ring with the distance between two oxygen atoms being as 2.99 Å and 3.16 Å, respectively as illustrated in FIG. 14. The active site of the binuclear enzyme tyrosinase has two copper ions complexed to an oxygen molecule in a peroxide oxidation state [$Cu^{II}$—$O_2$—$Cu^{II}$], which is key to the mechanism by which tyrosinase catalyzes the introduction of a hydroxyl group in the ortho position of the aromatic ring of a mono-phenol (such as tyrosine). (Decker et al. (2000) Angew. Chem. Int. Ed. 39:1591). The interactomic distances were reported as 3.56 Å for Cu—Cu. 1.90 Å for Cu—O and 1.41 Å for O—O. (Kitajima et al. (1989) J. Am. Chem. Soc. 111:8975). The parallel conformation of 1-(3-methyl-2,4-dimethoxyphenyl)-3-(2',4'-dihydroxyphenyl)-propane (UP302a, $IC_{50}$=0.24 μM) will perfectly chelate with both copper ions of the [$Cu^{II}$—$O_2$—$Cu^{II}$] complex from both the top and the bottom as illustrated in FIGS. 13 and 14. This dual chelation by the inhibitor to both copper ions at the active site will totally block the access of the substrate, such as L-Dopa to the enzyme, thus effectively inhibiting the function of the protein. Using the same approach, the isolated and synthetic diarylalkanes and diarylalkanols listed in Table 2 were analyzed. The results of this analysis indicated that the compounds with twisted or non-parallel conformations possessed either no ability or only a weak ability to inhibit the activity of tyrosinase.

From these studies it has been determined that the most effective diarylalkane inhibitors have two to three substituents on one aromatic ring and zero to multiple substituents on the second aromatic ring. The most favorable structures are those in which at least one aromatic ring is substituted in the 2 and 4-positions. Preferably the rings are 6-membered aromatic and/or heteroaromatic as demonstrated by two of the compounds isolated 1-(2-hydroxy-4-methoxyphenyl)-3-(2',3',4',5'-tetrahydro-bezo(b)dioxocin-8-yl)-1-propanol- $IC_{50}$=72 μM and 3-(5'-chloro-1'-methyl-1'-hydro-imidazol-2'-yl)-1-(2-hydroxy-4-methoxyphenyl)-1-propanol- $IC_{50}$=225 μM.

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a diarylalkane or a mixture comprised of two or more diarylalkanes.

The compositions of the present invention can be formulated as pharmaceutical compositions, which include other components such as a pharmaceutically and/or cosmetically acceptable excipient, an adjuvant, and/or a carrier. For example, compositions of the present invention can be formulated in an excipient that the host to be treated can tolerate. An excipient is an inert substance used as a diluent or vehicle for a therapeutic agent such as a diarylalkane or a mixture of diarylalkanes. Examples of such excipients include, but are not limited to water, buffers, saline, Ringer's solution, dextrose solution, mannitol, Hank's solution, preservatives and other aqueous physiologically balanced salt solutions. Non-aqueous vehicles, such as fixed oils, sesame oil, ethyl oleate, or triglycerides may also be used. Other useful formulations include suspensions containing viscosity-enhancing agents, such as sodium carboxymethylcellulose, sorbitol or dextran. Excipients can also contain minor amounts of additives, such as substances that enhance isotonicity and chemical stability. Examples of buffers include phosphate buffer, bicarbonate buffer, tris buffer, histidine, citrate, and glycine, or mixtures thereof, while examples of preservatives include, but are not limited to EDTA, disodium EDTA, BHA, BHT, vitamin C, vitamin E, sodium bisulfite, $SnCl_2$, thimerosal, m- or o-cresol, formalin and benzyl alcohol. Standard formulations can be either liquid or solids, which can be taken up in a suitable liquid as a suspension or solution for administration. Thus, in a non-liquid formulation, the excipient can comprise dextrose, human serum albumin, preservatives, etc., to which sterile water or saline can be added prior to administration.

In one embodiment of the present invention, the composition can also include an adjuvant or a carrier. Adjuvants are typically substances that generally enhance the biological response of a host to a specific bioactive agent. Suitable adjuvants include, but are not limited to, Freund's adjuvant, other bacterial cell wall components, aluminum, magnesium, copper, zinc, iron, calcium, and other metal ion based salts, silica, polynucleotides, toxoids, serum proteins, viral coat proteins, other bacterial-derived preparations, gamma interferon; block copolymer adjuvants; such as Hunter's Titermax adjuvant (Vaxcel™, Inc. Norcross, Ga.), Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated host. Suitable carriers include, but are not limited to, polymeric controlled release formulations, biodegradable implants, liposomes, bacteria, viruses, oils, esters, and glycols.

In one embodiment, the composition is prepared as a controlled release formulation, which slowly releases the composition of the present invention into the host. As used herein, a controlled release formulation comprises a composition of the present invention in a controlled release vehicle. Suitable controlled release vehicles will be known to those skilled in the art. Preferred controlled release formulations are biodegradable (i.e., bioerodible).

The therapeutic agents of the instant invention are preferably administered topically by any suitable means, known to those of skill in the art for topically administering therapeutic compositions including, but not limited to as an ointment, gel, lotion, or cream base, or as a toothpaste, mouth-wash, or coated on dental flossing materials or as an emulsion, as a patch, dressing or mask, a nonsticking gauze, a bandage, a swab or a cloth wipe. Example 18 describes the preparation of two cream formulations with an active content at 0.01% and 0.1% of a pure and/or mixture of diarylalkane(s) in the total weight of the formula. Such topical application can be locally administered to any affected area, using any standard means known for topical administration. A therapeutic composition can be administered in a variety of unit dosage forms depending upon the method of administration. For particular modes of delivery, a therapeutic composition of the present invention can be formulated in an excipient of the present invention. A therapeutic reagent of the present invention can be administered to any host, preferably to mammals, and more preferably to humans. The particular mode of administration will depend on the condition to be treated.

In one embodiment, a suitable ointment is comprised of the desired concentration of a single diarylalkane or a mixture of two or more diarylalkanes, that is an efficacious, nontoxic quantity generally selected from the range of 0.001% to 100% based on the total weight of the topical formulation, from 65 to 100% (preferably 75 to 96%) of white soft paraffin, from 0 to 15% of liquid paraffin, and from 0 to 7% (preferably 3 to 7%) of lanolin or a derivative or synthetic equivalent thereof. In another embodiment the ointment may comprise a polyethylene-liquid paraffin matrix.

In one embodiment, a suitable cream is comprised of an emulsifying system together with the desired concentration of a single diarylalkane or a mixture of two or more diarylalkanes as provided above. The emulsifying system is preferably comprised of from 2 to 10% of polyoxyethylene alcohols (e.g. the mixture available under the trademark Cetomacrogol™ 1000), from 10 to 25% of stearyl alcohol, from 20 to 60% of liquid paraffin, and from 10 to 65% of water; together with one or more preservatives, for example from 0.1 to 1% of N,N"-methylenebis[N'-[3-(hydroxymethyl)-2,5-dioxo-4-imidazolidinyl]urea] (available under the name Imidurea USNF), from 0.1 to 1% of alkyl 4-hydroxybenzoates (for example the mixture available from Nipa Laboratories under the trade mark Nipastat), from 0.01 to 0.1% of sodium butyl 4-hydroxybenzoate (available from Nipa Laboratories under the trade mark Nipabutyl sodium), and from 0.1 to 2% of phenoxyethanol.

In one embodiment, a suitable gel is comprised of a semi-solid system in which a liquid phase is constrained within a three dimensional polymeric matrix with a high degree of cross-linking. The liquid phase may be comprised of water, together with the desired amount of a single diarylalkane or a mixture of two or more diarylalkanes, from 0 to 20% of water-miscible additives, for example glycerol, polyethylene glycol, or propylene glycol, and from 0.1 to 10%, preferably from 0.5 to 2%, of a thickening agent, which may be a natural product, selected from the group including, but not limited to tragacanth, pectin, carrageen, agar and alginic acid, or a synthetic or semi-synthetic compound, selected from the group including, but not limited to methylcellulose and carboxypolymethylene (carbopol); together with one or more preservatives, selected from the group including, but not limited to for example from 0.1 to 2% of methyl 4-hydroxybenzoate (methyl paraben) or phenoxyethanol-differential. Another suitable base, is comprised of the desired amount of a single diarylalkane or a mixture of diarylalkanes, together with from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term soft paraffin as used above encompasses the cream or ointment bases white soft paraffin and yellow soft paraffin. The term lanolin encompasses native wool fat and purified wool fat. Derivatives of lanolin include in particular lanolins which have been chemically modified in order to alter their physical or chemical properties and synthetic equivalents of lanolin include in particular synthetic or semi-synthetic compounds and mixtures which are known and used in the pharmaceutical and cosmetic arts as alternatives to lanolin and may, for example, be referred to as lanolin substitutes.

One suitable synthetic equivalent of lanolin that may be used is the material available under the trademark Softisan™ known as Softisan 649. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No. 3 (1982), pp. 3-6.

The other substances mentioned hereinabove as constituents of suitable ointment or cream bases and their properties are discussed in standard reference works, for example pharmacopoeia. Cetomacrogol 1000 has the formula $CH_3(CH_2)_m(OCH_2CH_2)_nOH$, wherein m may be 15 or 17 and n may be 20 to 24. Butylated hydroxytoluene is 2,6-di-tert-butyl-p-cresol. Nipastat is a mixture of methyl, ethyl, propyl and butyl 4-hydroxybenzoates.

The compositions of the invention may be produced by conventional pharmaceutical techniques. Thus the aforementioned compositions, for example, may conveniently be prepared by mixing together at an elevated temperature, preferably 60-70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

The following examples are provided for illustrative purposes only and are not intended to limit the scope of the invention.

EXAMPLES

Example 1

Preparation of Organic Extracts from Dry Plants

Dried plant material was ground to a particle size of no larger than 2 mm and a portion (60 g) was transferred to an Erlenmeyer flask and extracted with 600 ml of methanol:dichloromethane (1:1). The mixture was shaken for one hour, filtered and the biomass was extracted again with methanol:dichloromethane (1:1) (600 ml). The organic extracts were combined and evaporated under vacuum to provide an organic extract from each plant material. Each extract (approximately 75 mg) was then dissolved in 1.5 ml DMSO to a concentration of 50 mg/ml, which was then stored in a −70° C. freezer. An aliquot of the extract solution was used for tyrosinase assay as described in Example 2.

Example 2

Tyrosinase Inhibition Assay

A tyrosinase inhibition assay was carried out using the method reported by Jones et al. (2002) Pigment. Cell Res. 15:335. Using this method, the conversion of L-Dopa, a substrate of tyrosinase, into dopachrome is followed by monitoring absorption at 450 nm. Tyrosinase was prepared in 50 mM potassium phosphate buffer, pH 6.8 (assay buffer) at 2000 U/ml and stored at −20° C. in 1 ml aliquots prior to use. For use in assays, stock enzyme solutions were thawed and diluted to 200 U/ml with assay buffer. A 2 mM working solution of substrate, L-DOPA, was prepared in assay buffer for each assay. Samples were dissolved in 10% DMSO (0.5 ml) and diluted to 5 ml with assay buffer. The reaction mixture consisted of 0.050 ml 2 mM L-DOPA, 0.050 ml 200 U/ml mushroom tyrosinase and 0.050 ml inhibitor. Reaction volume was adjusted to 200 µl with assay buffer. Assays were performed in 96 well Falcon 3097 flat-bottom microtiter plates (Beckton Dickinson, N.J.). Appearance of dopachrome was measured with a WALLAC 1420 Multilable Counter (Turku, Finland). Average velocity was determined from linear enzyme rate as measured by change in absorbance ($\Delta A_{450}$) at 450 nm per minute. Percent inhibition of tyrosinase by test samples was determined by comparison of absorbance of samples versus control using formula (I):

$$\text{(Negative control absorption−sample absorption)/Negative control absorption}\times 100 \quad (1)$$

The results are set forth in Table 1.

TABLE 1

Tyrosinase inhibitory activity of four plant extracts

| Plant Latin Name and Parts | Amount | Weight of the Organic Extract | Percent Inhibition of Tyrosinase (concentration mg/ml) |
|---|---|---|---|
| *Broussonetica kazinoki* whole plant | 20 g | 1.1 g | 68% (at 0.125 mg/ml) |
| *Rhus chinensis* cecidiums | 20 g | 12.8 g | 31% (at 0.125 mg/ml) |
| *Polygonum multiflorum* tubers | 20 g | 2.4 g | 43% (at 0.125 mg/ml) |
| *Dianella ensifolia* whole plant | 20 g | 1.7 g | 57% (at 0.125 mg/ml) |

Example 3

HTP Fractionation of Active Plant Extracts

Active organic extract (400 mg) was loaded onto a pre-packed, normal phase, flash column. (2 cm ID×8.2 cm, 10 g silica gel). The column was eluted using a Hitachi high throughput purification (HTP) system with a gradient mobile phase of (A) 50:50 EtOAc:hexane and (B) methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation. DMSO (1.5 mL) was used to dissolve the samples in each cell and a portion (100 μL) was taken for the tyrosinase inhibition assay in duplicate.

Example 4

Extraction, Separation and Purification of 1-(2-Methoxy-4-hydroxyphenyl)-3-(2'-hydroxy-5'-methoxyphenyl)-propane (1) from *Broussonetia kazinoki* (BK) (Whole Plant)

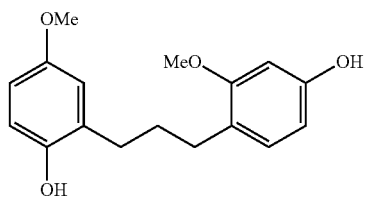

*Broussonetia kazinoki* (100 g whole plant) was ground and extracted three times with 800 ml of MeOH:DCM (1:2). Dried extract (6 g) was fractionated using a silica gel column with gradient solvent elution of hexane/ethyl acetate (50/50) to MeOH. Fractions were collected in 2 sets of 88 test tubes. LC/MS/PDA was utilized to check each of the fractions, which were then combined based on the similarity of their composition. The combined fractions were evaporated to remove solvent, dried and their tyrosinase inhibition activity measured as described in Example 2. It was found that fractions (P0346-HTP-F2-P0346-HTP-F4) were the most active and these fractions were combined and labeled as BK-F2-4. After solvent evaporation, BK-F2-4 was further separated on a pre-packed reverse phase column (C-18 column) using a water/MeOH gradient. Eighteen compound peaks were observed following separation. Fourteen reverse phase columns were performed and the similar fractions from each run were combined. One compound peak referred to as UP288 in the combined and enriched fraction showed strong tyrosinase inhibition activity (FIG. 4). After separation and purification with preparative HPLC, 6 mg of 1-(2-methoxy-4-hydroxyphenyl)-3-(2'-hydroxy-5'-methoxyphenyl)-propane (UP288) (1) was obtained. The structure of this compound was elucidated using MS and NMR spectroscopy (1H, $^{13}$C, HMQC and HMBC). FIG. 5 depicts the chemical structure and $^{13}$C-NMR spectrum of UP288. UP288 is an inhibitor of tyrosinase having activity comparable with that of kojic acid with $IC_{50}$ value of 24 μM. FIG. 6 illustrates tyrosinase inhibitory dose response curves and $IC_{50}$ values for UP288 and kojic acid.

1-(2-Methoxy-4-hydroxyphenyl)-3-(2'-hydroxy-5'-methoxyphenyl)-propane (UP288). Yield 0.006% (purity>96%, HPLC); UV $\lambda_{max}$: 281.0 nm; MS (Super Sound Ionization, Positive ion detection): m/z 289 (M+1, 100%); $^1$H-NMR (400 MHz, (CD$_3$)$_2$SO): δ 1.70 (2H, m, CH$_2$), 2.46 (4H, m, 2 CH$_2$), 3.68 (3H, s, OCH$_3$), 3.73 (3H, s, OCH$_3$), 6.26 (1H, q, H-5), 6.35 (1H, d, H-3), 6.55 (1H, q, H-14), 6.65 (1H, d, H-13), 6.72 (1H, d, H-16), 6.86 (1H, d, H-6), 8.69 (1H, s, OH), 9.20 (1H, s, OH); $^{13}$C-NMR (100 MHz, (CD$_3$)$_2$SO): Δ 28.5 (C-8), 31.6 (C-9), 34.5 (C-10), 55.0 (C-7), 55.6 (C-17), 98.9 (C-3), 106.4 (C-5), 112.4 (C-16), 115.2 (C-13), 119.7 (C-1), 119.8 (C-14), 120.3 (C-11), 120.4 (C-6), 132.9 (C-12), 144.6 (C-4), 147.2 (C-17) & 158.3 (C-7).

Example 5

Extraction, Separation and Purification of 1-(3-Methyl-2,4-dimethoxyphenyl)-3-(2',4'-dihydroxyphenyl)-propane (UP302a) (2) and 1-(3-methyl-2,4-dimethoxyphenyl)-3-(2',5'-dihydroxyphenyl)-propane (UP302b) (3) from *Dianella ensifolia* (P0389) (Whole Plant)

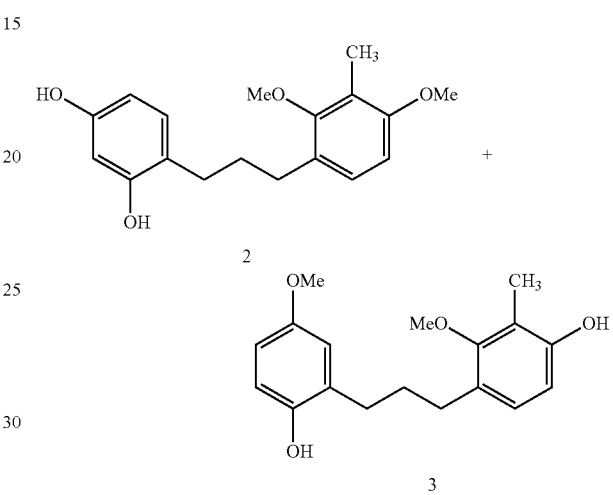

Figure 8:
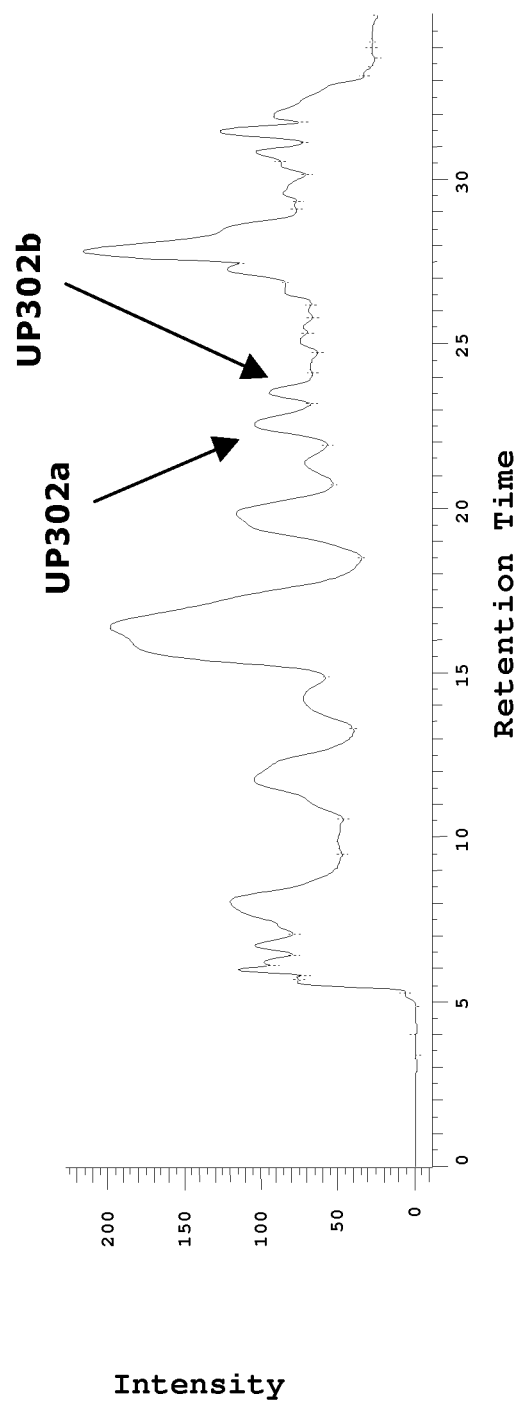
FIG. 8 depicts the HPLC/UV chromatogram of the enriched UP302 fraction after multiple column separations.
Figure 9:
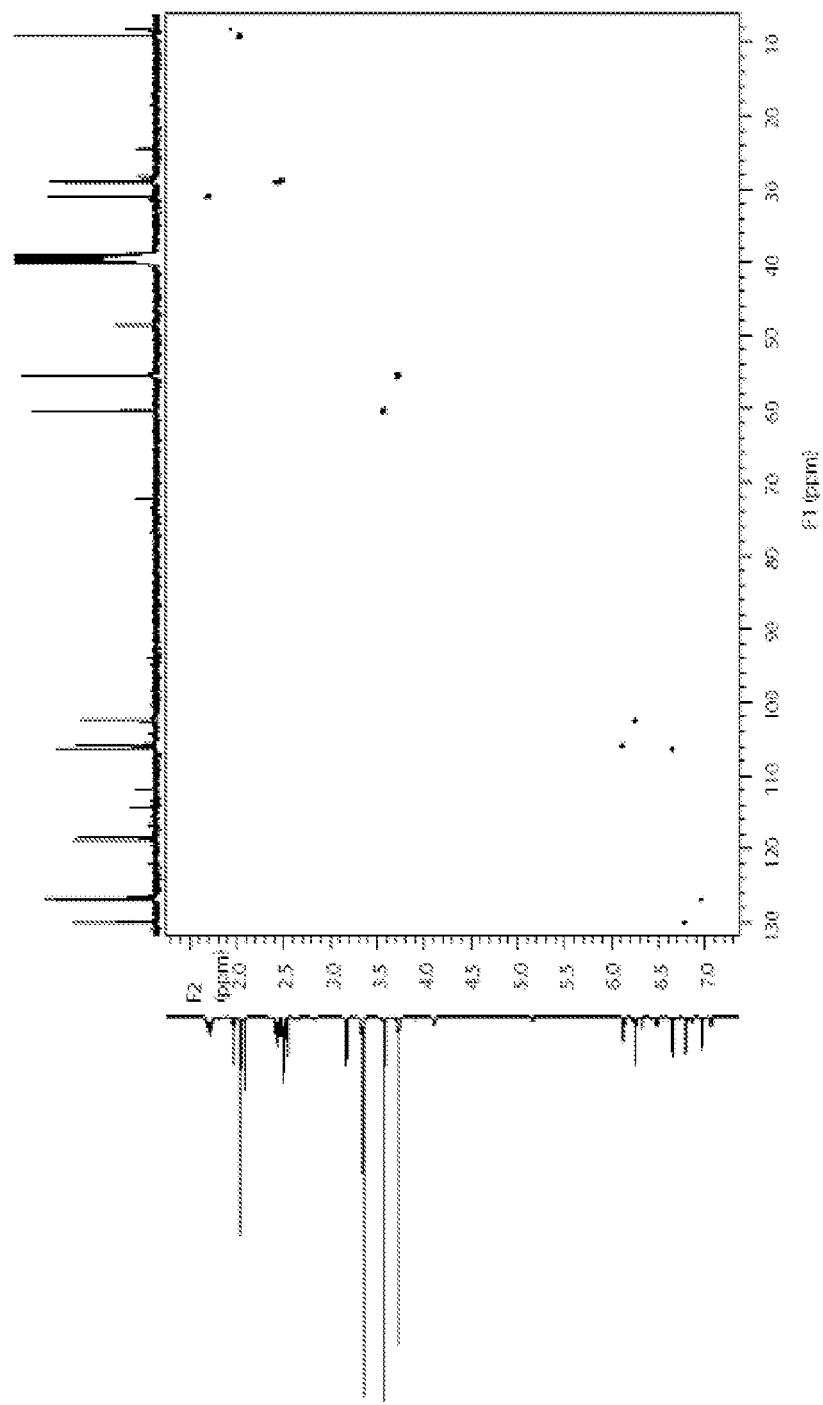
FIG. 9 depicts a gHSQC spectrum of UP302a (2), which illustrates the links between protons and carbons.

*Dianella ensifolia* (P0389, 300 g whole plant) was ground and extracted three times 800 ml of MeOH:DCM (1:2). Dried extract (5 g) was fractionated using a silica gel column with gradient solvent elution of hexane/ethyl acetate (50/50) to MeOH. Fractions were collected in 2 sets of 264 test tubes. LC/MS/PDA was utilized to check each of the fractions, which were then combined into 22 fractions based on the similarity of their composition. (FIG. 7). The combined fractions were evaporated to remove solvent, dried and their tyrosinase inhibition activity measured as described in Example 2. It was found that fractions P0389-HTP-F12, P0389-HTP-F13 and P0389-HTP-F14 were the most active and these fractions were combined and relabeled as DE-F12-14. After solvent evaporation, DE-F12—14 was further separated on a pre-packed reverse phase column (RP-column) using a water/MeOH gradient. Two major and eleven minor compound peaks were observed following separation. The compounds corresponding to each of these peaks were isolated following 7 additional separations on RP-columns. All of the compounds collected were dried and tested for tyrosinase inhibitory activity. Two of the eleven minor peaks referred to as UP302a and UP302b, respectively, exhibited strong tyrosinase inhibitory activity. (FIG. 8). After separation and purification, two active compounds were obtained: 1-(3-methyl-2,4-dimethoxyphenyl)-3-(2',4'-dihydroxyphenyl)-propane (UP302a, 10 mg) (2) and 1-(3-methyl-2,4-dimethoxyphenyl)-3-(2',5'-dihydroxyphenyl)-propane (UP302b, 6 mg) (3). The structures of these two compounds were elucidated using MS and NMR spectroscopy (1H, $^{13}$C, gHSQC and HMBC). FIG. 9 depicts the gHSQC spectrum of UP302a. Tyrosinase inhibition assays showed that UP302a was the most potent inhibitor with an $IC_{50}$ of 0.24 μM, while UP302b has an $IC_{50}$ of 12 μM.

1-(3-methyl-2,4-dimethoxyphenyl)-3-(2',4'-dihydroxyphenyl)-propane (UP302a) (2). Yield 0.02% (purity>98%, HPLC); UV $\lambda_{max}$: 279.8 nm; MS (Super Sound Ionization, Positive ion detection): m/z 303 (M+1, 100%); $^1$H-NMR (400 MHz, (CD$_3$)$_2$SO): δ 1.70 (2H, m, CH$_2$), 2.03 (3H, s, CH$_3$), 2.43 (2H, m, CH$_2$), 2.49 (2H, m, CH$_2$), 3.58 (3H, s, OCH$_3$), 3.73 (3H, s, OCH$_3$), 6.11 (1H, q, H-16), 6.25 (1H, d, H-14), 6.65 ($^1$H, d, H-5), 6.76 (1H, d, H-17), 6.97 (1H, d, H-6), 8.93 (1H, s, OH), 9.03 (1H, s, OH); $^{13}$C-NMR (100 MHz, (CD$_3$)$_2$SO): δ 28.8 (C-9), 29.3 (C-11), 31.1 (C-10), 55.3 (C-7), 55.9 (C-8), 102.4 (C-14), 105.8 (C-16), 106.1 (C-5), 118.4 (C-1), 118.6 (C-12), 126.9 (C-3), 127.0 (C-6), 130.1 (C-17), 155.7 (C-13), 156.2 (C-15), 156.3 (C-4) and 156.8 (C-2).

1-(3-methyl-2,4-dimethoxyphenyl)-3-(2',5'-dihydroxyphenyl)-propane (UP302b) (3). Yield 0.01% (purity>95%, HPLC); UV $\lambda_{max}$: 279.8 nm; MS (Super Sound Ionization, Positive ion detection): m/z 303 (M+1, 100%); $^1$H-NMR (400 MHz, (CD$_3$COCD$_3$): δ 1.82 (2H, m, CH$_2$), 2.07 (3H, s, CH$_3$), 2.52 (2H, m, CH$_2$), 2.56 (2H, m, CH$_2$), 3.63 (3H, s, OCH$_3$), 3.77 (3H, s, OCH$_3$), 6.64 (1H, q, H-15), 6.72 (1H, d, H-14), 6.64 (1H, d, H-5), 6.70 (1H, d, H-17), 7.00 (1H, d, H-6), 7.65 (1H, s, OH), and 7.69 (1H, s, OH).

Example 6

Large-scale Isolation of 1-(3-Methyl-2,4-dimethoxyphenyl)-3-(2',4'-dihydroxyphenyl)-propane (UP302A) (2) from *Dianella ensifolia* (DE) (Whole Plant)

*Dianella ensifolia* (4.3 kg whole plant) was collected, ground and extracted three times using a percolation extractor with methanol as the solvent. The extracts were combined and evaporated to remove the methanol. The crude extract was then suspended in water and partitioned with DCM. The layers were separated and the DCM layer was evaporated to provide 60 g of material. LC-MS/PDA analysis of both layers revealed that the majority of the UP302a was present in the DCM layer with only a minor amount present in the water layer. The DCM extract was fractionated on three separate silica gel columns eluting with a gradient of hexane-ETOAC. A total of 15 sub-fractions were obtained and analyzed by HPLC-MS/PDA. Targeted compound (UP302a) was found in fractions 6 to 9, which were combined to yield a total of 3 g of enriched UP302a. The enriched UP302a was further separated on an open column packed with CG-161 resin eluting with a water-MeOH gradient. A total of 23 fractions were collected with the UP302a eluting in fractions 15 to 21. Fractions 15-21 were then combined and the solvent was evaporated to yield 700 mg of a solid, which was further purified by preparative HPLC on a C-18 column to generate 30 mg of UP302a. The structure, tyrosinase inhibitory activity and purity of the purified product was confirmed by NMR, enzyme inhibition assay and LC-MS/PDA.

Example 7

Synthesis of Diarylalkanes by Sodium Borohydride Reduction of Substituted Chalcones A general method for the synthesis of diarylalkanes by sodium borohydride reduction of substituted chalcones is described below using the reduction of 2,4-dihydroxy)-3',4'-dimethoxychalcone (4) for purposes of illustration.

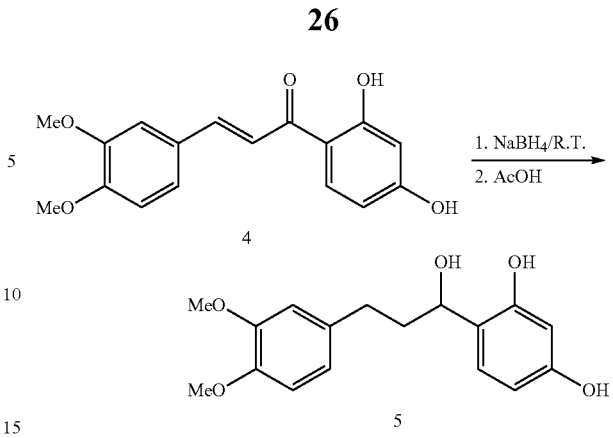

2,4-Dihydroxy-3',4'-dimethoxychalcone (4) (40 mg) was dissolved in 1-propanol (5 ml), followed by the addition of sodium borohydride (15 mg) and the mixture was allowed to react at room temperature for 2 hours. Upon completion of the reaction, 20% acetic acid (0.2 ml) was added and the mixture was heated at 80° C. for 5 minutes and cooled down. The mixture was then separated on a pre-packed C$_{18}$ column eluting with a MeOH/H$_2$O gradient to provide 1-(2,4-dihydroxyphenyl)-3-(3,4-dimethoxyphenyl)-1-propanol (5). The structure of compound (5) was confirmed by MS, UV spectroscopy, 1D and 2D $^1$H-NMR.

1-(2,4-dihydroxyphenyl)-3-(3',4'-dimethoxyphenyl)-1-propanol (5). Yield 60% (purity>98%, HPLC); UV $\lambda_{max}$: 278.5 nm; MS (Super Sound Ionization, Positive ion detection): m/z 305 (M+1, 100%); $^1$H-NMR (400 MHz, (CD$_3$)$_2$SO): δ 1.93 (2H, m, CH$_2$), 2.60 (2H, m, CH$_2$), 4.49 (1H, m, CH—OH), 3.78 (3H, s, OCH$_3$), 3.80 (3H, s, OCH$_3$), 6.28 (1H, q, H-5), 6.31 (1H, d, H-3), 6.98 (1H, d, H-6), 6.71 (1H, q, H-5'), 6.77 (1H, d, H-2'), 6.83 (1H, d, H-6').

Using the above-described general method the following compounds were reduced to their corresponding alcohols: 2,4-dihydroxy-2'-hydroxychalcone, 2'-hydroxy-4'-methoxy-2,4-dimethoxy-chalcone, 4'-hydroxy-4-hydroxy-chalcone, 2',4'-dihydroxy-2-hydroxy-chalcone, 2',4'-dihydroxy-3,4-dimethoxy-chalcone, 2',4',6'-trimethoxy-3,4-dimethoxychalcone and 2'-hydroxy-4'-methoxy-3,4,5-trimethoxy-chalcone to provide 1-(2,4-dihydroxyphenyl)-3-(2'-hydroxyphenyl)-1-propanol, 1-(2-hydroxy-4-methoxyphenyl)-3-(2',4'-dimethoxyphenyl)-1-propanol, 1-(4-hydroxyphenyl)-3-(4'-hydroxyphenyl)-1-propanol, 1-(2,4-dihydroxyphenyl)-3-(2'-hydroxyphenyl)-1-propanol, 1-(2,4-dihydroxyphenyl)-3-(3',4'-di-methoxyphenyl)-1-propanol, 1-(2,4,6-trimethoxyphenyl)-3-(3',4'-dimethoxyphenyl)-1-propanol and 1-(2-hydroxy-4-methoxyphenyl)-3-(3',4',5'-trimethoxyphenyl)-1-propanol.

Example 8

Synthesis of Substituted Diphenylpropanols by Sodium Borohydride Reduction of Substituted Diarylpropanones A general method for the synthesis of substituted diphenylpropanols by sodium borohydride reduction of substituted diarylpropanones is described below using the reduction of 1-(2-hydroxy-5-methoxyphenyl)-3-(2',4'-dimethoxyphenyl)-1-propanone (6) for purposes of illustration.

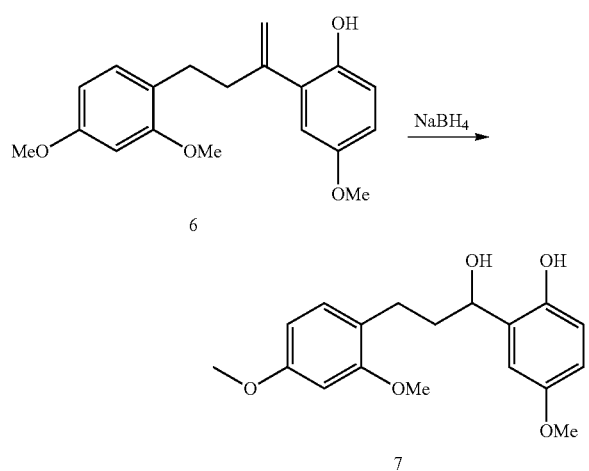

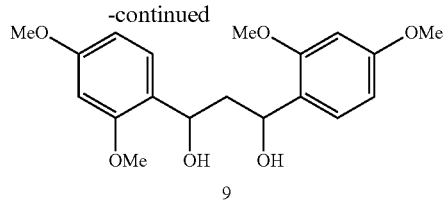

1-(2-hydroxy-5-methoxyphenyl)-3-(2',4'-dimethoxyphenyl)-1-propanone (6) (5 mg) was dissolved in 1-propanol (1 ml), followed by the addition of sodium borohydride (2 mg) and the mixture was allowed to react at room temperature for 5 hours. Upon completion of the reaction, 20% acetic acid (0.2 ml) was added to neutralize the excess sodium borohydride. The reaction mixture was then separated on a prepacked $C_{18}$ column eluting with a MeOH/H$_2$O gradient to provide 1-(2-hydroxy-5-methoxyphenyl)-3-(2',4'-dimethoxyphenyl)-1-propanol (7).

Following the above-described general synthetic procedure the following diarylalkane compounds were reduced: 1-(2-hydroxy-4,6-dimethoxyphenyl)-3-(3'-methoxy-4'-hydroxyphenyl)-1-propanone, 3-(5'-benzyloxy-4'-methoxy-2'-methylphenyl)-1-(2-hydroxy-4,5-dimethoxyphenyl)-1-propanone, 1-(2-hydroxy-4-methoxyphenyl)-3-(2',3',4',5'-tetrahydro-bezo(b)dioxocin-8'-yl)-1-propanone and 3-(5'-chloro-1'-methyl-1'-hydro-imidazol-2'-yl)-1-(2-hydroxy-4-methoxyphenyl)-1-propenone to provide 1-(2-hydroxy-4,6-dimethoxyphenyl)-3-(3'-methoxy-4'-hydroxyphenyl)-1-propanol, 3-(5'-benzyloxy-4'-methoxy-2'-methylphenyl)-1-(2-hydroxy-4,5-dimethoxyphenyl)-1-propanol, 1-(2-hydroxy-4-methoxy-phenyl)-3-(2',3',4',5'-tetrahydro-bezo(b)dioxocin-8-yl)-1-propenol and 3-(5'-chloro-1'-methyl-1'-hydro-imidazol-2'-yl)-1-(2-hydroxy-4-methoxy-phenyl)-1-propenol, respectively.

Example 9

Synthesis of 1,3-Bis(2,4-dimethoxyphenyl)-propan-1,3-diol (9)

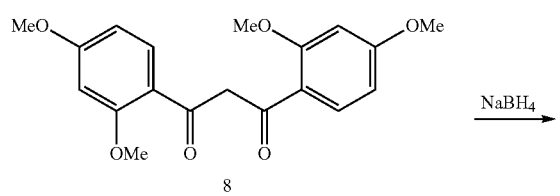

1,3-Bis(2,4-dimethoxyphenyl)-propan-1,3-dione (8) (5 mg) was dissolved in 1-propanol (1 ml), followed by the addition of sodium borohydride (3 mg) and the mixture was allowed to react at room temperature for 3 hours. Upon completion of the reaction, 20% acetic acid (0.2 ml) was added to neutralize the excess sodium borohydride. The mixture was then separated on a pre-packed $C_{18}$ column eluting with a MeOH/H$_2$O gradient to provide 1,3-bis(2,4-dimethoxyphenyl)-propan-1,3-diol (9).

Example 10

Synthesis of 1-(2,4,6-Trihydroxyphenyl)-3-(3'-hydroxy-4'-methoxyphenyl)-1-propanol (11) from Neohesperidin

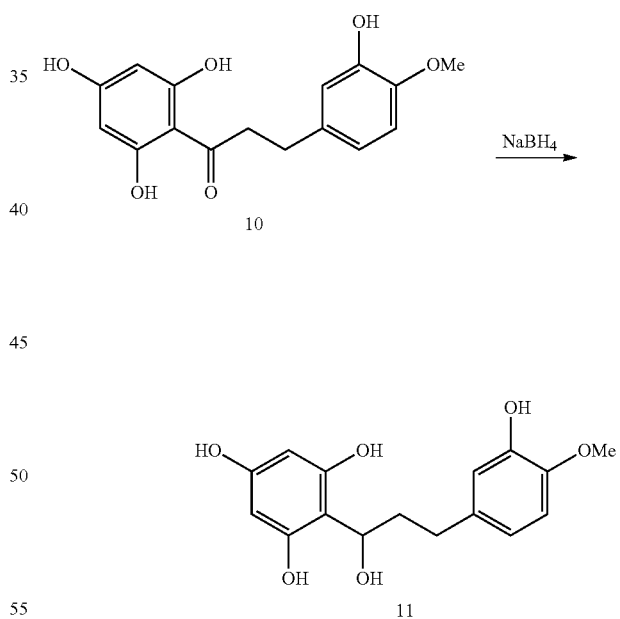

Neohesperidin is a glycoside of dihydrochalcone. A total weight of 100 mg of neohesperidin was suspended in 10 ml of 1 N HCl and heated at 80° C. for 2 hours. The hydrolyzed product (10) was cooled down and extracted with ethyl acetate (3×10 ml). The ethyl acetate layers were combined, evaporated to remove ethyl acetate and dissolved in 1-propanol (5 ml). Sodium borohydride (25 mg) was added to the propanol solution and stirred at room temperature for 2 hours. After the completion of the reaction, the mixture was separated on a pre-packed $C_{18}$ column eluting with a MeOH/H$_2$O gradient to provide 1-(2,4,6-trihydroxyphenyl)-3-(3'-hydroxy-4'-methoxyphenyl)-1-propanol (11).

Example 11

Extraction, Purification and Structure Modification of Butrin to Synthesize 1-(2,4-Dihydroxyphenyl)-3-(3',4'-dihydroxyphenyl)-1-propanol (14)

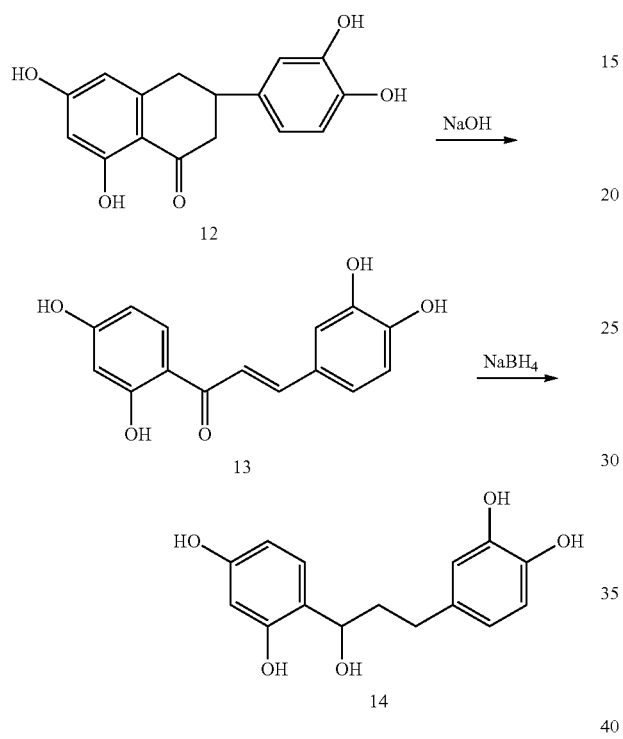

Butrin is a high content flavanone-glycoside that has been extracted with methanol from the dried flowers of *Butea frondosa* and purified by multiple reverse phase column chromatographic separations. After removing sugars by hydrolysis with HCl, butin (12) was produced and purified by RP-HTP (1.5% yield from the whole plant). Butin was then treated with 10% sodium hydroxide at 80° C. to obtain butein (13), which was reduced with sodium borohydride to obtain 1-(2,4-dihydroxyphenyl)-3-(3',4'-dihydroxyphenyl)-1-propanol (14) ($IC_{50}$=250 nM).

Example 12

Synthesis of 1-(2,4-dihydroxyphenyl)-3-(3'-methoxy-4'-hydroxyphenyl)-1-propanol (19)

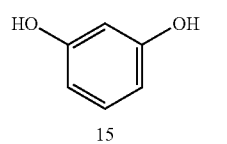

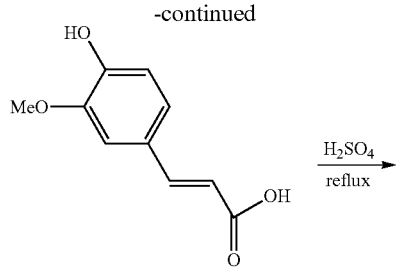

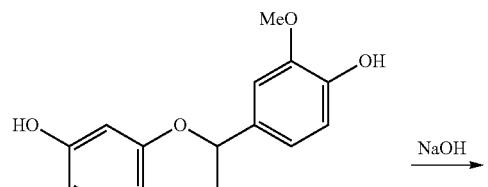

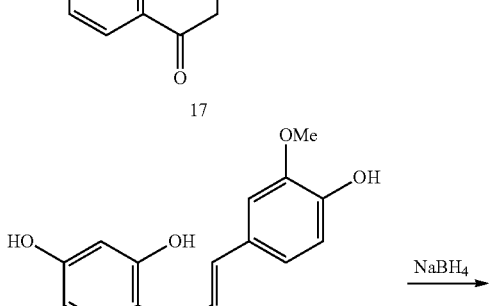

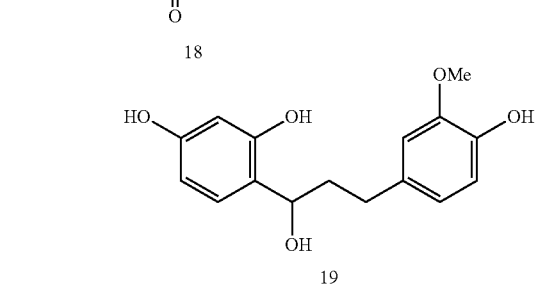

Resorcinol (15), 3-methoxy-4-hydroxy-cinnamic acid (16) and $H_2SO_4$ (5%) were refluxed in THF for 4 hours to provide 7,4'-dihydroxy-3'-methoxy flavanone (17) (90% yield). The product, 7,4'-dihydroxy-3'-methoxy flavanone (17) was then treated with 10% sodium hydroxide at 80° C. for 1 hour, followed by reduction with sodium borohydride in propanol to provide, as confirmed LC-MS/PDA detection, 1-(2,4-dihydroxyphenyl)-3-(3'-methoxy-4'-hydroxyphenyl)-1-propanol (19). The crude product exhibits quite strong tyrosinase inhibitory activity. The mixture was further purified by HTP.

Example 13

$IC_{50}$ Measurements of Tyrosinase Inhibition by Synthetic Diarylalkanes

Inhibition of tyrosinase by synthetic diarylalkanes was measured using the method described in Example 2. The $IC_{50}$ value of each sample was calculated using kinetics software to verify that the reaction was linear at a specified time and concentration. Using the methods described in Examples 7-12a total of 24 compounds were synthesized and evaluated for their ability to inhibit tyrosinase. The results are set forth in Table 2.

TABLE 2

$IC_{50}$ values of synthetic diarylalkanes and/or diarylalkanols

| Compound Name | Tyrosinase Inhibition ($IC_{50}$) |
|---|---|
| 1-(2,4-dihydroxyphenyl)-3-(3',4'-dihydroxyphenyl)-1-propanol | 0.5 μm |
| 1-(2,4-dihydroxyphenyl)-3-(3',4'-dimethoxyphenyl)-1-propanol | 0.85 μm |
| 1-(2,4-dihydroxyphenyl)-3-(2'-hydroxyphenyl)-1-propanol | 0.7 μm |
| 1-(2,4-dihydroxyphenyl)-3-(2'-methoxyphenyl)-1-propanol | 3 μm |
| 1-(2,4-dihydroxyphenyl)-3-(4'-methoxyphenyl)-1-propanol | 6 μm |
| 1-(2,4,6-trihydroxyphenyl)-3-(4'-aminophenyl)-1-propanol | 8 μm |
| 1-(2,4-dihydroxyphenyl)-3-phenyl-1-propanol | 8 μm |
| 1-(2,4-dihydroxyphenyl)-3-(3'-methoxy-4'-hydroxyphenyl)-1-propanol | 8.5 μm |
| 1-(2-hydroxy-4-methoxyphenyl)-3-(3',4',5'-trimethoxyphenyl)-1-propanol | 11 μm |
| 1-(2-hydroxy-4-methoxyphenyl)-3-(2',4'-dimethoxyphenyl)-1-propanol | 25 μm |
| 1-(2-hydroxy-5-methoxyphenyl)-3-(3',4'-dimethoxyphenyl)-1-propanol | 30 μm |
| 1-(2,4-dihydroxyphenyl)-2-(4'-methoxyphenyl)-1-ethanol | 77 μm |
| 1-(2-hydroxy-4-methoxyphenyl)-3-(2',3',4',5'-tetrahydro-benzo(b)dioxocin-8'-yl)-1-propanol | 72 μm |
| 3-(5'-chloro-1'-methyl-1'-hydro-imidazol-2'-yl)-1-(2-hydroxy-4-methoxyphenyl)-1-propanol | 225 μm |
| 1-(4-hydroxyphenyl)-3-(4'-hydroxyphenyl)-1-propanol | 305 μm |
| 1-(2-hydroxy-4,6-dimethoxyphenyl)-3-(3'-methoxy-4'-hydroxyphenyl)-1-propanol | 375 μm |
| 1-(2,4-dihydroxyphenyl)-2-(3',4'-dimethoxyphenyl)-1-ethanol | 431 μm |
| 1,4-bis-(3,4-dihydroxyphenyl)-2,3-dimethylbutane | 700 μm |
| 1-(2-hydroxy-5-methoxyphenyl)-3-(2',4'-dimethoxyphenyl)-1-propanol | 1000 μm |
| 1-(2,4-dihydroxyphenyl)-2-(2',4'-dichlorophenyl)-1-ethanol | 1000 μm |
| 1-(2,4,6-trihydroxyphenyl)-3-(3'-hydroxy-4'-methoxyphenyl)-1-propanol | 1200 μm |
| 1,3-bis(2,4-dimethoxyphenyl)-propan-1,3-diol | 1200 μm |
| 1-(2,4,6-trihydroxyphenyl)-3-(3'-hydroxy-4'-methoxyphenyl)-1-propanol | 1200 μm |
| 1-(2,4,6-trimethoxyphenyl)-3-(3',4'-dimethoxyphenyl)-1-propanol | 1500 μm |

Example 14

Enzyme Inhibition Kinetics

Figure 10:
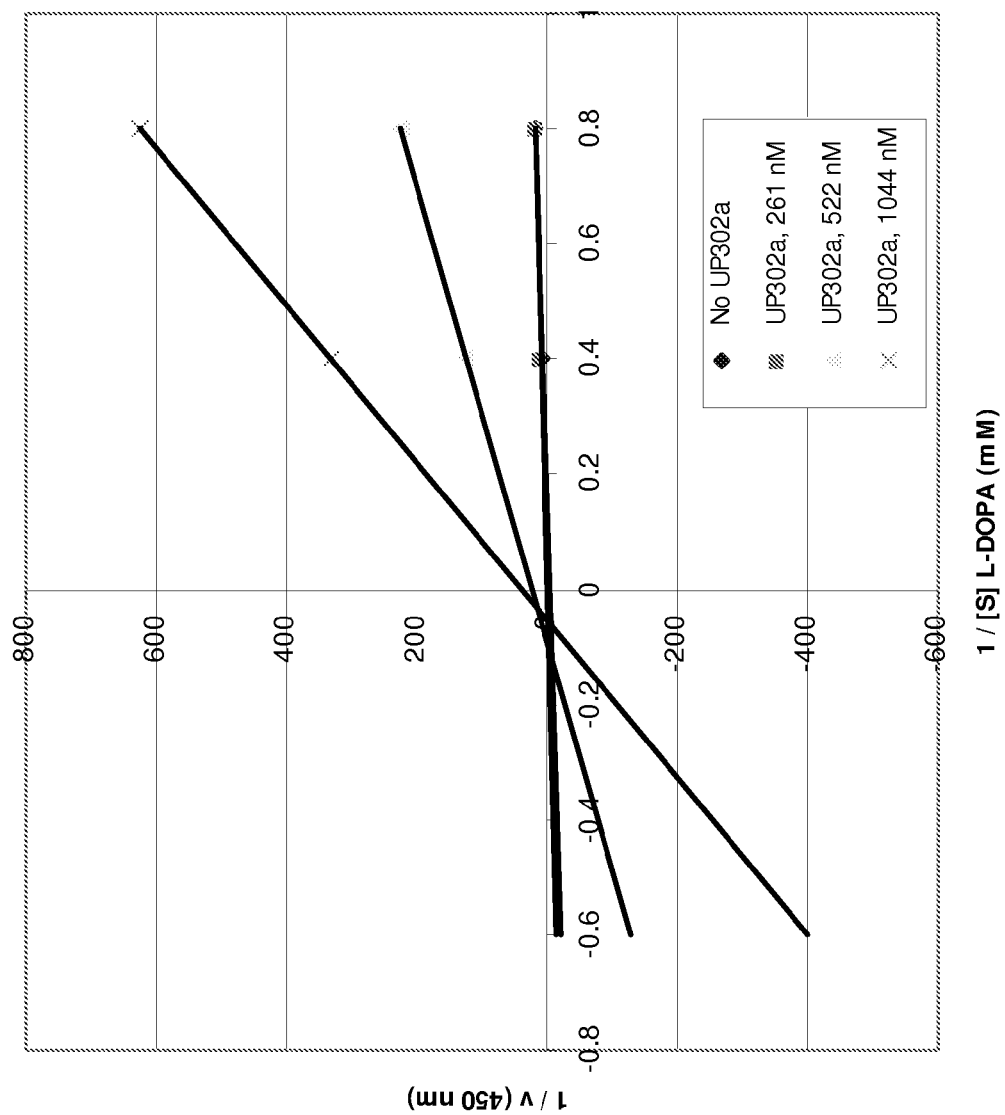
FIG. 10 illustrates graphically inhibition of the activity of tyrosinase at various concentrations of inhibitor UP302a and substrate L-DOPA. This kinetic study revealed that UP302a is a competitive inhibitor of the tyrosinase enzyme.

Using the method described in Example 2, the inhibition of tryosinase was evaluated at different concentrations (0, 261, 522, 1044 nM) of an inhibitor (UP302a) using L-DOPA at concentrations of 0.75, 1.25, and 2.5 mM as the substrate. As shown in FIG. 10, it was found that UP302a is a competitive inhibitor with potent and long lasting inhibitory effect. Tyrosinase activity was not resumed for several days after incubation with UP302a. In contrast, tyrosinase activity was totally restored after only 1 hour following incubation with kojic acid.

Example 15

Inhibition of Melanin Production from B-16 Cell Line

The inhibition of melanin production was evaluated using two different assays. In the first assay, the inhibition of melanin production was evaluated without induction by β-MSH; whereas in the second assay the inhibition of melanin production was measured with β-MSH induction in cell culture medium. Briefly, B16 F1 cells (ATCC# CRL-622) were grown to confluency and then seeded at 40,000 cells per well. The cells were allowed to attach overnight at 37° C. in a humidified environment containing 5% $CO_2$. On day 2, inhibitors were added to the cells at concentrations ranging from 0-1000 μM in triplicate and allowed to incubate for four days. The amount of β-MSH required to induce melanin formation was determined by the addition of hormone at concentrations ranging from 0-1000 nM in ten-fold increments. Once the proper β-MSH concentration was determined, cells were seeded as above, allowed to attach overnight and then co-incubated with tyrosinase inhibitors at concentrations ranging from 0-1000 μM. Color development was visually monitored each morning. After the development of color, 200 μl of cell supernatant was removed from each well and absorbance was measured at 450 nm. The resulting readings were used to determine the $IC_{50}$ for melanin formation in the cell assay with and without β-MSH induction. For an initial comparison of cell toxicity, the 250 μM treated wells were used to perform a lactate dehydrogenase assay (LDH). LDH is a metabolic enzyme that leaks out of damaged or dead cells. The enzyme converts a chromophore in the presence of $NAD^+$ to yield a color change that can be monitored spectrophotometrically.

The results of this assay revealed that all of the natural inhibitors tested (UP288, UP302a, and UP302b) are at least as good, if not better inhibitors than kojic acid. There were some differences in the $IC_{50}$ values under the two sets of conditions Inhibition by kojic acid improved from an $IC_{50}$ of 170 μM for the endogenous experiment to an $IC_{50}$ of 67 μM in the induced experiment. Of the inhibitors tested relative to kojic acid, compound UP302b was only one that that showed an increase in $IC_{50}$ under the two sets of conditions increasing from an $IC_{50}$ of 5.2 μM to an $IC_{50}$ of 34 μM. The $IC_{50}$'s measured for inhibition of tyrosinase were relatively the same for all of the compounds tested with the exception of the two compounds UP302 and UP302b, which had low $IC_{50}$'s of 0.2 μM and 0.3 μM, respectively, compared to 28 μM and 5.2 μM in the endogenous assay and 40 μM and 34 μM in the induced assay. These differences may be due to decreased cell penetration by UP302a (2) and UP302b (3), as compared to the other inhibitors. This is overcome, however by the strength of their inhibition of the enzyme.

Table 3 provides the results of these two assays for inhibitors UP288 and UP302a relative to kojic acid.

Example 16

Cell Toxicity Assay

The compound treated wells were used to perform a lactate dehydrogenase assay (LDH). LDH is a metabolic enzyme that leaks out of damaged or dead cells. The enzyme converts a chromophore in the presence of $NAD^+$ to yield a color change that can be monitored spectrophotometrically. The cytotoxicity was examined at a concentration of 250 µM. At this concentration none of these compounds are significantly more cytotoxic than kojic acid. It should be noted however, that cytotoxicity at only one concentration (250 µM) was tested. As shown in the Table 3, UP288 (1) and UP302a (2) showed moderate cytotoxicity, which were comparable with kojic acid.

TABLE 3

Inhibition of mushroom tyrosinase and melanin formation in mouse B16 F1 cells by isolated compounds and comparison of cell toxicity

| Compound | Tyrosinase Inhibition $IC_{50}$ (µM) | Endogenous Melanin Inhibition $IC_{50}$ (µM) | MSH Induced Melanin Inhibition $IC_{50}$ (µM) | Cell Toxicity (LDH) |
|---|---|---|---|---|
| UP288 | 24.0 | 108 | 105 | 0.315 |
| UP302a | 0.24 | 28 | 40 | 0.265 |
| Kojic acid | 29 | 170 | 67 | 0.260 |

Example 17

Molecular Mechanics (MM2) Calculation

Molecular mechanics calculations were performed using Chem3D software for purposes of energy minimization and determination of the most stable 3-D conformation. The following parameters were used: Step interval=2.0 fs, frame interval=10 fs, terminate after 10,000 steps, heating/cooling rate=1.000 Kcal/atom/PS, target temperature=3000K. Properties: pi bond orders and steric energy summary. All natural and synthetic compounds and other diarylalkane and diarylalkanol structures were analyzed. It was found that the most potent tyrosinase inhibitor—1-(3-methyl-2,4-dimethoxyphenyl)-3-(2,4-dihydroxyphenyl)-propane (UP302a (2), $IC_{50}$=0.24 µM)—isolated from whole plants of *Dianella ensifolia* (L.) DC. has a very unique 3-dimentional conformation in which the two aromatic rings were superimposed on each other. The minimized total energy for the conformation is −4.7034 KJ/Mol. The distance between the two aromatic rings was 3.28 Å. The phenolic hydroxyl groups on the first aromatic ring were right above the two methoxyl groups on the second aromatic ring with the distance between two oxygen atoms being 2.99 and 3.16 Å, respectively as illustrated in FIGS. 12-14. This intramolecular parallel conformation allows this compound to perfectly chelate both copper ions of the binuclear enzyme when it is in the peroxide form $[Cu^{II}-O_2-Cu^{II}]$ from both the top and the bottom.

Example 18

Formulation of the Diarylalkane Composition into a Cream

UP302a is comprised of a substituted diarylpropane as the major active component. These compounds are soluble in high polarity solvents including, but not limited to ethanol, propylene glycol and ethylene glycol. They can be formulated with a pharmaceutically and/or cosmetically acceptable excipient, an adjuvant, and/or a carrier. Examples of such excipients include, but are not limited to water, buffers, saline, Ringer's solution, dextrose solution, mannitol, Hank's solution, preservatives and other aqueous physiologically balanced salt solutions. Nonaqueous vehicles including, but not limited to fixed oils, sesame oil, ethyl oleate, or triglycerides may also be used. Other useful formulations include, but are not limited to suspensions containing viscosity enhancing agents, including, but not limited to sodium carboxymethylcellulose, sorbitol, or dextran. Excipients can also contain minor amounts of additives or preservatives, such as antioxidants that enhance color and chemical stability. UP302 also can be prepared in a liposome formulation to increase its skin penetration or as a controlled release formulation, which slowly releases the composition of the active ingredient into the host.

UP302a is preferably administered topically as an ointment, gel, lotion, or cream base or as an emulsion, a patch, dressing or mask, a nonsticking gauze, a bandage, a swab or a cloth wipe. Such topical application can be locally administered to any affected area, using any standard means known for topical administration. UP302 can be administered to both humans and animals.

A therapeutic composition of UP302a can be administered in a variety of unit dosage forms depending upon the method of administration and targeted indications. An efficacious, nontoxic quantity is generally recommended in the range of 0.01% to 5% based on total weight of the topical formulation. Two different concentrations of UP302a (0.01% and 0.5% by weight) were formulated in creams as illustrated in Tables 4 and 5. To prepare these creams the diarylalkane was dissolved in water at room temperature and homogenized in a blender until it was fully dispersed in solution (approximately 5 minutes) to yield a composition A. At room temperature and without stifling or agitating, Ultrez-21 carbomer was added to the homogenized solution by sprinkling it onto the surface and allowing it to fully wet (no white areas visible) and fall into the solution. With gentle stifling, the solution was then heated to 40° C. and glycerin was added and the composition was mixed for an additional 5 minutes to provide Composition B. At 40° C., Composition A is added to Composition B and the composition is mixed well until homogenous (approximately 5 minutes). The resulting emulsion is cooled to 30° C. and the pH adjusted to approximately 5.5 (5.3 to 5.7) by titrating with neutralizer while stifling with a stir bar and/or spatula. The emulsion became highly viscous due to the neutralization-induced conformational change of the carbomer. Upon stifling the emulsion will achieved a suitable viscosity for an emulsion cream. The composition was mixed until uniform, poured into clean storage vessels and stored at 2° C. to 8° C.

TABLE 4

Composition of 0.01% Diarylalkane Cream

| Phase | Ingredient | % (w/w) | Weight (g) |
|---|---|---|---|
| Aqueous | Water, Purified | 85.00 | 12 |
| | Diarylalkane (UP302a) | 0.01 | 0.0015 |
| | Ultrez 21 Carbomer | 0.50 | 0.075 |
| | Glycerin | 8.00 | 1.2 |

TABLE 4-continued

Composition of 0.01% Diarylalkane Cream

| Phase | Ingredient | % (w/w) | Weight (g) |
|---|---|---|---|
| Oil | PEG-7 Glyceryl Cocoate | 3.00 | 0.45 |
|  | Caprylic/Capric Triglyceride | 2.67 | 0.4 |
| PH Neutralizer | Sodium Hydroxide (18% w/v), Molecular Biology Grade | 0.00 | 0.0 |
| SUM | 7 Ingredients | 100 | 15 |

TABLE 5

Composition of 0.1% UP302 Cream

| Phase | Ingredient | % (w/w) | Weight (g) |
|---|---|---|---|
| Aqueous | Water, Purified | 84.00 | 12.6 |
|  | Diarylalkane (UP302a) | 0.1 | 0.0015 |
|  | Ultrez 21 Carbomer | 0.50 | 0.075 |
|  | Glycerin | 8.00 | 1.2 |
| Oil | PEG-7 Glyceryl Cocoate | 3.00 | 0.45 |
|  | Caprylic/Capric Triglyceride | 2.67 | 0.4 |
| PH Neutralizer | Sodium Hydroxide (18% w/v), Molecular Biology Grade |  |  |
| SUM | 7 Ingredients | 99.7 | 15 |

The invention claimed is:

1. An isolated and purified compound having the following structure (2):

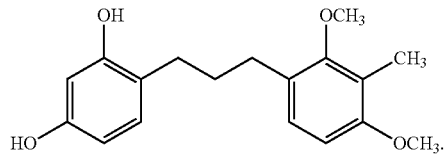

(2)

2. The compound of claim 1, wherein the compound is isolated from one or more plants of the *Dianella* plant genus.

3. The compound of claim 1, wherein the compound comprises a purity of greater than 98% as determined by HPLC analysis.

4. The compound of claim 1, wherein the compound is obtained by organic synthesis.

5. A composition comprising the compound of claim 1 and a physiologically acceptable carrier, excipient, adjuvant or combinations thereof.

6. The composition of claim 5, wherein the composition is formulated for topical administration.

7. The composition of claim 5, wherein the composition is formulated as an ointment, gel, lotion, cream, paste or emulsion.

8. The composition of claim 5, wherein the composition comprises an effective skin lightening amount of the compound.

* * * * *